United States Patent [19]
Anderson et al.

[11] Patent Number: 5,948,656
[45] Date of Patent: Sep. 7, 1999

[54] TIA-1 BINDING PROTEINS AND ISOLATED COMPLEMENTARY DNA ENCODING THE SAME

[75] Inventors: Paul J. Anderson, Belmont; Qingsheng Tian, Cambridge, both of Mass.

[73] Assignee: Dana-Farber Cancer Institute, Boston, Mass.

[21] Appl. No.: 08/795,303

[22] Filed: Feb. 4, 1997

Related U.S. Application Data

[60] Division of application No. 08/318,947, Oct. 6, 1994, Pat. No. 5,798,245, which is a continuation-in-part of application No. 08/133,530, Oct. 7, 1993, abandoned.

[51] Int. Cl.$^6$ .............................. C12N 9/00; C12N 9/12; C12N 1/21; C07H 21/04
[52] U.S. Cl. .................. 435/183; 435/194; 435/252.3; 435/254.11; 435/320.1; 536/23.2
[58] Field of Search ............................ 435/194, 320.1, 435/252.3, 183; 536/23.5, 23.2

[56] References Cited

U.S. PATENT DOCUMENTS

| | | | | |
|---|---|---|---|---|
| 5,283,173 | 2/1994 | Fields et al. | ................................. | 435/6 |
| 5,298,407 | 3/1994 | Anderson et al. | ..................... | 435/69.1 |

FOREIGN PATENT DOCUMENTS

WO/A93/01314  1/1993  WIPO.

OTHER PUBLICATIONS

Le Guellec, R. et al. "Cloning by differential screening of a Xenopus cDNA that encodes a kinesin–related protein" Molecular and Cellular Biology (Jun. 1991), vol. 11, No. 6, pp. 3395–3398.

Lewis, S.A. et al. "Sequence of a cDNA clone encoding mouse glial fibrillary acidic protein: structural conservation of intermediate filaments" Proceedings of the National Academy of Sciences, USA (May 1984), vol. 81, pp. 2743–2746.

Proc. Natl. Acad. Sci. USA, vol. 89, issued Sep. 1992, Kawakami et al, "Identification And Functional Characterization of a TIA–1–Related Nucleolysin", pp. 8681–8685.

Nature, vol. 340, issued Jul. 20, 1989, Fields et al, "A Novel Genetic System To Detect Protein–Protein Interactions", pp. 245–246.

L.J. Ko and C. Prives, "p53: puzzle and paradign", *Genes & Dev.*, 10:1054–1072 (1996).

J.C. Reed, "Double identity for proteins of the BcL–2 family", *Nature*, 387:773–776 (1997).

Q. Tian et al., "Fas–activated Serine/Threonine Kinase (FAST) Phosphorylates TIA–1 during Fas–mediated Apoptosis", *J. Exp.Med.*, 182:865–874 (1995).

Pir2 Database Entry G01873 Accession number G01873; Dec. 21, 1990; Niedergang, C. XP002048659 *the whole document*.

Taupin J–L et al; "Identification of candidate substrates for TIA—1–mediated cytotoxicity." Experimental Biololgy 94, Parts I and II, Anaheim, California, USA, Apr. 24–28, 1994. FASEB Journal 8 (4–5). 1994 A206. ISSN: 0892–6638, XP002048658 *abstract No. 1187*.

*Primary Examiner*—Kawai Lau
*Attorney, Agent, or Firm*—Sughrue, Mion, Zinn Macpeak & Seas, PLLC

[57] ABSTRACT

Complementary DNA (cDNA) has been isolated having a sequence that encodes a polypeptide that binds TIA-1 in a double transformation. In one embodiment, the polypeptide is immunologically reactive with the monoclonal antibody produced by the hybridoma designated ATCC #HB-11721. Specific cDNA sequences have been determined and amino acid sequences have been deduced therefrom.

53 Claims, 24 Drawing Sheets

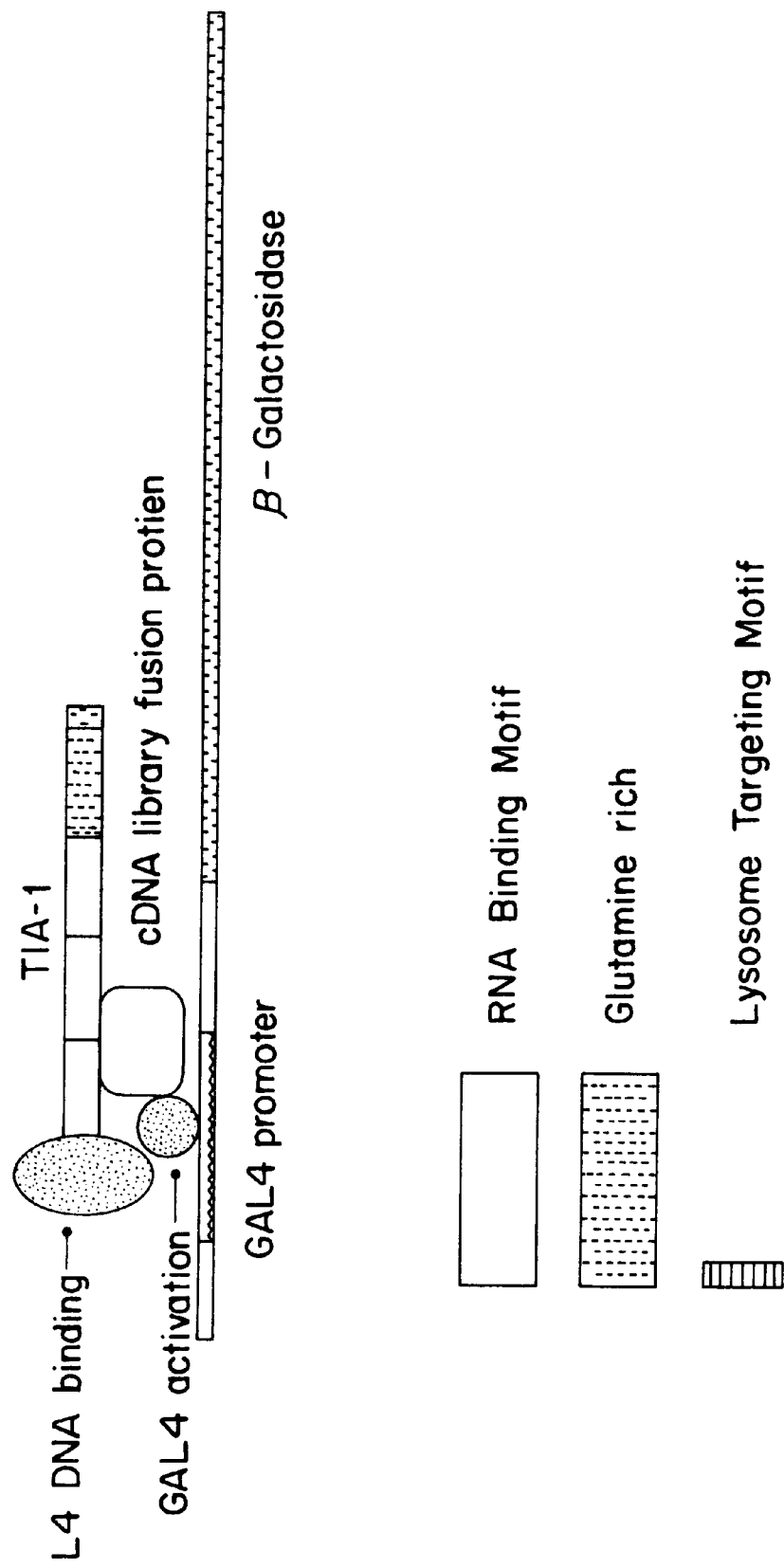

FIG. 3A

```
TIABP1
  1                     21
  CCA CCA AAC CCA AAA AAA GAG ATC TGG AAT TCG GAT CCT CGA GGC
                                       41
                   61                                    81
  CAC GAA GGC CGC GGG CTC CGG AGG GAA GTC CCG AGA CAA AGG GAA
                  101                                   121
  GCG CCG CCG CCG CCC CGC TCG GTC CTC CAC CTG TCC GCT ACG
         141                                      161
  CTC GCC GGG GCT GCG GCC CGA GGG ACT TTG AAC ATG TCG GGG
                                              met ser gly
         181                                      201                   221
  ATC GCC CTC AGC AGA CTC GCC CAG GAG AGG AAA GCA TGG AGG AAA
  ile ala leu ser arg leu ala gln glu arg lys ala trp arg lys
```

FIG. 3B

```
241                                      261
GAC CAC CCA TTT GGT TTC GTG GCT GTC CCA ACA AAA AAT CCC GAT
asp his pro phe gly phe val ala val pro thr lys asn pro asp 281                                      301
GGC ACG ATG AAC CTC ATG AAC TGG GAG TGC ATT CCA GGA AAG
gly thr met asn leu met asn trp glu cys ala ile pro gly lys 321                                      341
AAA GGG ACT CCG TGG GAA GGA GGC TTG TTT AAA CTA CGG ATG CTT
lys gly thr pro trp glu gly gly leu phe lys leu arg met leu 361                      381              401
TTC AAA GAT GAT TAT CCA TCT TCG CCA CCA AAA TGT AAA TTC GAA
phe lys asp asp tyr pro ser ser pro pro lys cys lys phe glu 421                      441
CCA CCA TTA TTT CAC CCG AAT GTG TAC CCT TCG GGG ACA GTG TGC
pro pro leu phe his pro asn val tyr pro ser gly thr val cys
```

FIG. 3C

```
                                481
CTG TCC ATC TTA GAG GAG GAC AAG GAC TGG AGG CCA GCC ATC ACA
leu ser ile leu glu glu asp lys asp trp arg pro ala ile thr
        501                 521
ATC AAA CAG ATC CTA TTA GGA ATA CAG GAA CTT CTA AAT GAA CCA
ile lys gln ile leu leu gly ile gln glu leu leu asn glu pro
    541                 561                         581
AAT ATC CAA GAC CCA GCT CAA GCA GAG GCC TAC ACG ATT TAC TGC
asn ile gln asp pro ala gln ala glu ala tyr thr ile tyr cys
                601                             621
CAA AAC AGA GTG GAG TAC GAG AAA AGG GTC CGA GCA CAA GCC AAG
gln asn arg val glu tyr glu lys arg val arg ala gln ala lys
    641                             661
```

FIG. 3D

```
     AAG TTT GCG CCC TCA TAA GCA GCG ACC TTG TGG CAT CGT CAG AAG    (SEQ ID NO:2)
     lys phe ala pro ser ***
              681                          701
721  GAA GGG ATT GGT TTG GCA AGA ACT TGT TTA CAA CAT AAT CTA AAG
              741                          761
781  TTG CTC CAT ACA TGA CTA GTC ACC TGG GGG GGT TGG GCG GGC GCA
              821                          801
     TCT TCC ATT GCC GCC GCG GGT GTG CGT CTC GAT TCG CTG AAT TGC
                                           841
     CCG TTT CCA TAC AGG GTC TCT TCC TTC GGT CTT TTG TAT TTT TGA
              861                          881
     TTG TTA TGT AAA ACT CGC TTT TAT TTT AAT ATT GAT GTC AGT ATT
901           921                          941
     TCA ACT GCT GTA AAA TTA TAA ACT TTT ATA CTT GGG TAA GTC CCC
```

FIG. 3E

```
                                         961
AGG CGA GGT TCC TCG CTC TGG GAT GCA GGC ATG CTT CTC ACG TGC
         1001                                   1021
AGC TGT CAA CTT GGC CTC AGC TGG CTG TAT GGA AAT GCA CCC TCC
         1041                      1061
CTC CTG CGC TCC TCT CTA GAA CCG GCT AGA ACC TGG GCT GTG CTG
1081                     1101                            1121
CTT TTG AGC CTC AGA CCC CAG GGC AGC ATC TCG GTT CTG CGC CAC
                   1141                      1161
TTC CTT TGT GTT TAT ATG GCG TTT TGT CTG TGT TGC TGT TTA GAG
1181                     1201
TAA ATA AAA CTG TTT ATA TAA AAA AAA AAA AAA AAA
```

(SEQ ID NO:1)

FIG.4A

```
TIABP2
GGC GGA CTC GGT GGC TAG CCG ATG AGG AGG CCG CGG GAA CCC GGC         48
                        Pro Met Arg Arg Pro Arg Gly Glu Pro Gly
                         1                   5                  10

CCC CGG GCC CCG AGA CCG ACT GAG GGA GCG ACC TGC GCA GGG CCC GGG     96
Pro Arg Ala Pro Arg Pro Thr Glu Gly Ala Thr Cys Ala Gly Pro Gly
                 15                  20                  25

GAG TCA TGG TCT CCA TCA CCC AAC ATG CTT CGA GTC CTG CTC TCT        144
Glu Ser Trp Ser Pro Ser Pro Asn Met Leu Arg Val Leu Leu Ser
         30                  35                  40

GCT CAG ACC TCC CCT GCT CGG TCT GGC CTG CTG CTG ATC CCT CCA        192
Ala Gln Thr Ser Pro Ala Arg Leu Ser Gly Leu Leu Leu Ile Pro Pro
         45                  50                  55

GTA CAG CCC TGC TGT TTG GGG AGC AAA TGG GGG GAC CGG CCT GTT        240
Val Gln Pro Cys Cys Leu Gly Ser Lys Trp Gly Asp Arg Pro Val
         60                  65                  70

GGA GGA GGC CCC AGT GCA GGT CCT GTG CAA GGA CTG CAG CGG CTT CTG   288
Gly Gly Gly Pro Ser Ala Gly Pro Val Gln Gly Leu Gln Arg Leu Leu
 75                  80                  85                  90

GAA CAG GCG AAG AGC CCT GGG GAG CTG CTG CTG CGC TGG CTG GGC CAG AAC 336
Glu Gln Ala Lys Ser Pro Gly Glu Leu Leu Leu Arg Trp Leu Gly Gln Asn
         95                 100                 105
```

FIG.4B

```
CCC AGC AAG GTG CGC GCC CAC CAC TAC TCG GTG GCG CTT CGT CTG         384
Pro Ser Lys Val Arg Ala His His Tyr Ser Val Ala Leu Arg Arg Leu
            110                 115                 120

GGC CAG CTC TTG GGG TCT CGG CCA CGG CCC CCT GTG GAG CAG GTC         432
Gly Gln Leu Leu Gly Ser Arg Pro Arg Pro Pro Val Glu Gln Val
        125                 130                 135

ACA CTG CAG GAC TTG AGT CAG CTC ATC ATC CGA AAC TGC CCC TCC TTT     480
Thr Leu Gln Asp Leu Ser Gln Leu Ile Ile Arg Asn Cys Pro Ser Phe
            140                 145                 150

GAC ATT CAC ACC ATC CAC GTG TGT CTG CAC CTT GCA GTC TTA CTT GGC     528
Asp Ile His Thr Ile His Val Cys Leu His Leu Ala Val Leu Leu Gly
            155                 160                 165             170

TTT CCA TCT GAT GGT CCC CTG GTG TGT GCC CTG GAA CAG GAG CGA AGG     576
Phe Pro Ser Asp Gly Pro Leu Val Cys Ala Leu Glu Gln Glu Arg Arg
            175                 180                 185

CTC CGC CTC CCT CCG AAG CCA CCT CCC CCT TTG CAG CCC CTT CTC CGA     624
Leu Arg Leu Pro Pro Lys Pro Pro Pro Pro Leu Gln Pro Leu Leu Arg
        190                 195                 200

GGT GGG CAA GGG TTG GAA GCT GCT CTA AGC TGC CCC CGT TTT CTG CGG     672
Gly Gly Gln Gly Leu Glu Ala Ala Leu Ser Cys Pro Arg Phe Leu Arg
        205                 210                 215
```

FIG.4C

```
TAT CCA CGG CAG CAT CTG ATC AGC AGC CTG GCA GAG GCA AGG CCA GAG    720
Tyr Pro Arg Gln His Leu Ile Ser Ser Leu Ala Glu Ala Arg Pro Glu
220                 225                 230

GAA CTG ACT CCC CAC GTG ATG GTG CTC CTG GCC CAG CAC CTG GCC CGG    768
Glu Leu Thr Pro His Val Met Val Leu Leu Ala Gln His Leu Ala Arg
235                 240                 245                 250

CAC CGG TTG CGG GAG CCC CAG CTT CTG GAA GCC ATT GCC CAC TTC CTG    816
His Arg Leu Arg Glu Pro Gln Leu Leu Glu Ala Ile Ala His Phe Leu
        255                 260                 265

GTG GTT CAG GAA ACG CAA CTC AGC AGC AAG GTG GTA CAG AAG TTG GTC    864
Val Val Gln Glu Thr Gln Leu Ser Ser Lys Val Val Gln Lys Leu Val
    270                 275                 280

CTG CCC TTT GGG CGA CTG AAC TAC CTG CCC CTG GAA CAG CAG TTT ATG    912
Leu Pro Phe Gly Arg Leu Asn Tyr Leu Pro Leu Glu Gln Gln Phe Met
285                 290                 295

CCC TGC CTT GAG AGG ATC CTG GCT CGG GAA GCA GGG GTG GCA CCC CTG    960
Pro Cys Leu Glu Arg Ile Leu Ala Arg Glu Ala Gly Val Ala Pro Leu
300                 305                 310

GCT ACA GTC AAC ATC TTG ATG TCA CTG TGC CAA CTG CGG TGC CTG CCC    1008
Ala Thr Val Asn Ile Leu Met Ser Leu Cys Gln Leu Arg Cys Leu Pro
315                 320                 325                 330
```

FIG.4D

```
TTC AGA GCC CTG CAC TTT GTT TTT TCC CCT GGC TTC ATC AAC TAC ATC    1056
Phe Arg Ala Leu His Phe Val Phe Ser Pro Gly Phe Ile Asn Tyr Ile
        335                 340                 345

AGT GGC ACC CCT CAT GCT CTG ATT GTG CGT CGC TAC CTC TCC CTG CTG    1104
Ser Gly Thr Pro His Ala Leu Ile Val Arg Arg Tyr Leu Ser Leu Leu
        350                 355                 360

GAC ACG GCC GTG GAG CTC GAG CTC CCA GGA TAC CGG GGT CCC CGC CTT    1152
Asp Thr Ala Val Glu Leu Glu Leu Pro Gly Tyr Arg Gly Pro Arg Leu
        365                 370                 375

CCC CGA AGG CAG CAA GTG GAG CTG ATC TTT CCC CAG CCT CTC ATC ACC GAC    1200
Pro Arg Arg Gln Gln Val Glu Leu Ile Phe Pro Gln Pro Leu Ile Thr Asp
        380                 385                 390

CGT GCC CGC CGC TGC AAG TAC AGT CAC AAG GAC ATA GCT GAG GGG TTG    1248
Arg Ala Arg Arg Cys Lys Tyr Ser His Lys Asp Ile Ala Glu Gly Leu
        395                 400                 405                 410

CGC CAG CTG CTG GGG GAG GAG AAA TAC CGC CAG GAC CTG ACT GTG CCT    1296
Arg Gln Leu Leu Gly Glu Glu Lys Tyr Arg Gln Asp Leu Thr Val Pro
        415                 420                 425

CCA GGC TAC TGC ACA GAC TTC CTG TGC GCC AGC TCT GGT GCT    1344
Pro Gly Tyr Cys Thr Asp Phe Leu Cys Ala Ser Ser Gly Ala
        430                 435                 440
```

FIG. 4E

```
GTG CTT CCC GTG AGG ACC CAG GAC CCC TTC CTG CCA TAC CCA CCA AGG    1392
Val Leu Pro Val Arg Thr Gln Asp Pro Phe Leu Pro Tyr Pro Pro Arg
        445                 450                 455

TCC TGC CAG CCA CAG GGC CAG GCT GCC TCT AGC GCC ACT CGA GAC CCT    1440
Ser Cys Pro Gln Gly Gln Ala Ala Ser Ser Ala Thr Arg Asp Pro
    460                 465                 470

GCC CAG AGG GTG CTG GTG TTG CGG GAA CGC ATT CAT TTC TGC CGG         1488
Ala Gln Arg Val Leu Val Leu Arg Glu Arg Trp His Phe Cys Arg
475                 480                 485                 490

GAC GGC CGG GTG CTG GGC TCG AGG GCC CTG AGG GAG CGG CAC CTA         1536
Asp Gly Arg Val Leu Gly Ser Arg Ala Leu Arg Glu Arg His Leu
        495                 500                 505

GGC CTG ATG GGC TAC CAG CTC CTG CCG CTA CCC TTC GAG GAA CTG GAG    1584
Gly Leu Met Gly Tyr Gln Leu Leu Pro Leu Pro Phe Glu Glu Leu Glu
        510                 515                 520

TCC CAG AGA GGC GGG CTG CAG CTC AAG AGC TAC CTG AGG CAG AAG CTC    1632
Ser Gln Arg Gly Gly Leu Gln Leu Lys Ser Tyr Leu Arg Gln Lys Leu
    525                 530                 535

CAA GCC CTG GGC CTG CGC TGG GGG CCT GAA GGG GGC TGA GGG GAT GAT    1680
Gln Ala Leu Gly Leu Arg Trp Gly Pro Glu Gly Gly
540                 545                 550
```

FIG.4F

GTG GGG TTC AGG ATG GCC CCC CCA TGG GGG GTG GAT GAT TTG CAC TTT  1728

GGT TCC CTG TGT TTT GAT TTC TCA TTA AAG TTC CTG GCC TTC AAA AAA  1776

(SEQ ID NO:3)

(SEQ ID NO:4)

TIABP IS STRUCTURALLY RELATED TO UBIQUITIN CONJUGATING ENZYMES

```
            1
TIABP       MSGIALSRLAQERKAWRKDHPFGFVAVPTKNPDGTMNLMNWECAIPGKKGTPWEGGLFKL
HHR6B       MSTPARRRLMRDFKRLQEDPPVGVSGAPSEN               NIMQWNAVIFGPEGTPFEDGTFKL
Human E2    MSTPARRRLMRDFKRLQEDPPVGVSGAPSEN               NIMQWNAVIFGPEGTPFEDGTFKL
HHR6A       MSTPARRRLMRDFKRLQEDPPAGVSGAPSEN               NIMVWNAVIFGPEGTPFGDGTFKL
Dhr6        MSTPARRRLMRDFKRLQEDPPTGVSGAPTDN               NIMIWNAVIFGPHDTPFEDGTFKL
rhp6        MSTTARRRLMRDFKRMQQDPPAGVSASPVSD               NVMLWNAVIIGPADTPFEDGTFKL
RAD6        MSTPARRRLMRDRKRMKEDAPPGVSASPLPD               NVMVWNAMIIGPADTPYEDGTFRL 61
TIABP       RMLFKDDYPSSPPKCKFEPPLFHPNVYPSGTVCLSILEEDKDWRPAITIKQILLGIQELL
HHR6B       LIEFSEEYPNKPPTVRFLSKMFHPNVYADGSICLDIL         QNRWSPTYDVSSILTSIQSLL
Human E2    VIEFSEEYPNKPPTVRFLSKMFHPNVYADGSICLDIL         QNRWSPTYDVSSILTSIQSLL
HHR6A       TIEFTEEYPNKPPTVRFVSKMFHPNVYADGSICLDIL         QNRWSPTYDVSSILTSIQSLL
Dhr6        TIEFTEEYPNKPPTVRFVSKVFHPNVYADGGICLDIL         QNRWSPRYDVSAILTSIQSLL
rhp6        VLSFDEQYPNKPPLVKFVSTMFHPNVYANGELCLDIL         QNRWSPTYDVAAILTSIQSLL
RAD6        LLEFDEEYPNKPPHVKFLSEMFHPNVYANGEICLDIL         QNRWTPTYDVASILTSIQSLF 121
TIABP       NEPNIQDPAQAEAYTIYCQNRVEYEKRVRAQAKKFAPS                          (SEQ ID NO:5)
HHR6B       CEPNPNSPANSQAAQLYQENKREYEKREYEKRVSAIVEQSWNDS                    (SEQ ID NO:6)
Human E2    DEPNPNSPANSQAAQLYQENKREYEKREYEKRVSAIVEQSWNDS                    (SEQ ID NO:7)
HHR6A       DEPNPNSPANSQAAQLYQENKREYEKREYEKRVSAIVEQSWRDC                    (SEQ ID NO:8)
Dhr6        SDPNPNSPANSTAAQLYKENRREYEKRVKACVEQSFID                          (SEQ ID NO:9)
rhp6        NDPNNASPANAEAAQLHRENKKEYVRRVRKTVEDSWES                          (SEQ ID NO:10)
RAD6        NDPNPASPANVEAATLFKDHKSQYVKRVKETVEKSWEDDMDDMDDDDDDDDDDDDDDEAD   (SEQ ID NO:11)
```

FIG. 5

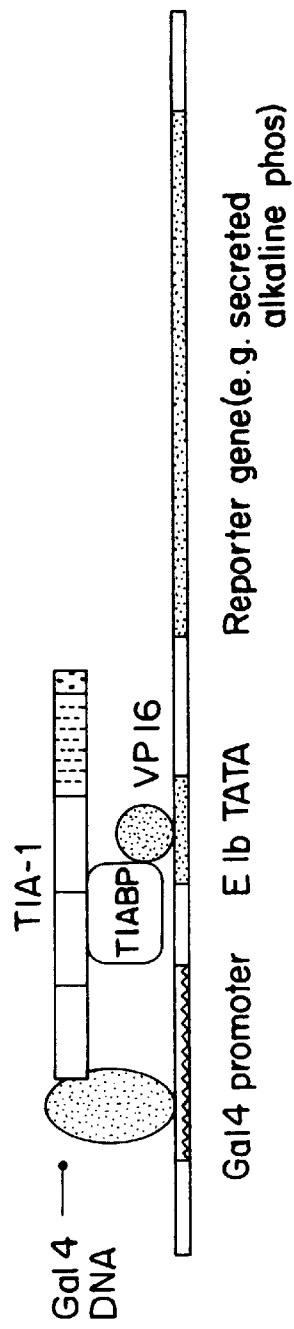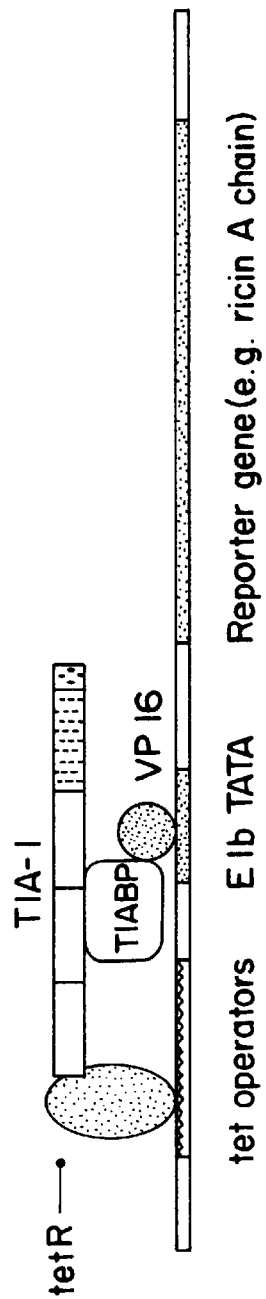

FIG. 8A

```
TIAK    (64)  PSKWGDRPVGGGPSAGPVQGLQRLLQAKSPGELLRWLGRNPSKVRAHHYSVALRRLGQLLGS
HSV-1  (104)  VAVTNIGAGSDGGT-AVVAFGGTPRR----(44)----GGEGDPVGPAEFVSDDRSSDSDSD
HSV-2   (60)  FVAISNVAAGGNGRT-AVVALGGTSG----(50)----ARGGAEKDVGAAESWSDG-------
cdc2          MENYQKVEKIGEGTY-GVVYKARHKL-------------SGRIVAMKKIRLEDESEG-------
cdk2          MENFQKVEKIGEGTY-GVVYKARNKL-------------TGEVVALKKIRLDTETEG-------
src    (267)  ESLRLEVKLGQGCR-GEVWMGIWNG--------------TTRVAIKTLKPGTM----------
Consensus:                   G_G__G_Y                                      A_K
                              I                                            II TIAK          RPRPPPVEQVTLQDLSQLIIRNCPSFDIHTIHVCLHLAVLLGFPSDGPLVCALEQERRLRLP
HSV-1         DSEDTDSETISHASSDVSGGATYDDALDSDSSSDDSLQIDGPVCRPWSNDTAPLDVCPGTPG
HSV-2         --PSSDSETEDSDSSDEDTGSSGETLSRSSSIWAAGATDDDDSDSRSDDSVQPDVVVRRR
cdc2          VPSTAIREISLLKEVNDENNRSNCVRLLDILHAESKLYLVFEFLDMKLKKYMDRISFTGATS
Cdk2          VPSTAIREISLLKELNHPNI----VKLLDVIHTENKLYLVFEFLHQDLKKFMDASALTGIPL
src           SPEAFLQEAQVMKKLRHEKLVQLYAVVSEEPIYIVTEYMSKGSLLDFLKGETGKYLRLPQLV
Consensus:             E                I
                      III              IV
```

FIG. 8B

```
TIAK        *
            PKPPPPLQPLLRGGQGLEAALSCPRFLRYPRQHLI----------------------------
HSV-1       PGADAGGPSAVDPHAPTPEAGAGLAADP----------------AVARDDAEGLSDPRPRLG
HSV-2       W-SDGPAPVAFPKPRRPGDSPGNPGLGAGTGPGSATDPRASADSDSAAHAAAPQADVAPVLDSQPTVG
cdc2        LDPRLVQKFTYQLVNGVNF---------------------------------------------
Cdk2        PLIKSYLFQLLQGLAR------------------------------------------------
src         DMAAQIASGMAY---------------------------------------------------
Consensus:

TIAK          *****           *       *     ***              *        *   ** ***
            SSLAEARPEELTPHVMVLLAQHLARHRLREPQLLEAIAHFLVVQETQLSSKVV----QKL-VLPFGRLNYL
HSV-1       TGTAYPVPLELTPENAEAVARFLGDAVNREPALMLEYFCRCAREETKRVPPRTFGSPPRLTEDDFGLLNY
HSV-2       TDPGYPVPLELTPENAEAVARFLGDAVDREPALMLEYFCRCAREESKRVPPRTFGSAPRLTEDDFGLLNT
cdc2        CHSRRIIHRDLKPQNLLIDKEG------------------------------------NLKLADFGLARSFGV
cdk2        CHSHRVLHRDLKPQNLLINTEG------------------------------------AIKLADFGLARAFGV
src         VERMNYVHRDLRAANILVGENL------------------------------------VCKVADFGLARLIE
Consensus:    DL   N                                                    DFG
              VI                                                         VII
```

FIG. 8C

```
TIAK       PLEQQFMPCLERILAREAGVAPLATVNILMSLCQLRCLPFRALHFVHSPGFINYISGTPHALIVRRTLSL
HSV-1      ALVEMQRLCLDVPPVPPNAYMP------------------------------------------------
HSV-2      ALAEMRRLCLDLPPVPPNAYTP------------------------------------------------
cdc2       PLRNYTHEIVTL----------------------------------------------------------
cdk2       PVRTYTHEVVTL----------------------------------------------------------
src        DNEYTARQGAKFPI--------------------------------------------------------
Consensus:     *         **

TIAK       LDTAVELELPGYRGPRLPRRQQVPIFPQPLITDRARCKYSHKDIVAEGLRQLLGEEKYRQDLTVPPG
HSV-1      -YYLREYVTRLVNGFKPLVSRSARLYRILGVLVHLRIRTREASFEEWLRSKEVALDFGLTERLREHE
HSV-2      -YHLREYATRLVNGFKPLVRRSARLYRILGILVHLRIRTREASFEEWMRSKEVDLDPGLTERLREHE
cdc2       WYRAPEVLL-------------------------GSRHYSTGVDIWSVGCIFAEMIRRSPLFPGDSEID
cdk2       WYRAPEILL-------------------------GSKYYSTAVKIWSLGCIFAEMVTRRALFPGDSEID
src        KWTAPEAA--------------------------LYGRFTIKSDVWSRGILLTELTTKGRVPYPGMVNR
Consensus:    AE                                                  D  G
              VIII                                                   IX TIAK       YCTDFLLCASSSGAVLPVRTQDPFLPYPPRSCPQGQAASSATTRDPAQRVVLVLRERWHFSRDGRVLL (SEQ ID NO: 16)
HSV-1      AQLVILAQALDHYDCLIHSTPHTLVERGLQSALKYEEFYLKRFGGHYMESVFQMYTRIAGFLACRAT  (SEQ ID NO: 17)
HSV-2      AQLMILAQALNPYDCLIHSTPNTLVERGLQSALKYEEHYLKRHGGHYMESVHQMYTRIAGPLACRAT  (SEQ ID NO: 18)
cdc2       EIFKIFQVLGTPNEEVWPGVTLLQDYKSTFPRWKRMDLYHKVVPNGEEDAIELLSAMLVYDPAHR    (SEQ ID NO: 19)
cdk2       QLFRIFRTLGTPDEVVWPGVTSMPDYKPSFPKWARQDF-SKVVPPLDEDGRSLLSQMLHYDPNKR    (SEQ ID NO: 20)
src        ---------------------PESLHDLMCQCWRKEPEERPTF                           (SEQ ID NO: 21)
Consensus:                                                                     R
                                                                                 L
```

FIG. 9A
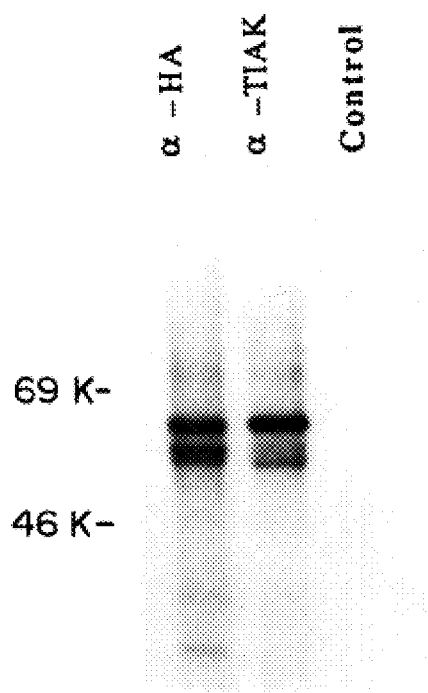
FIG. 9B
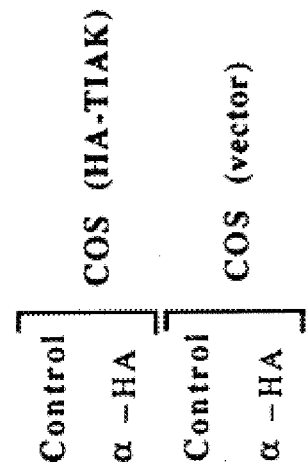
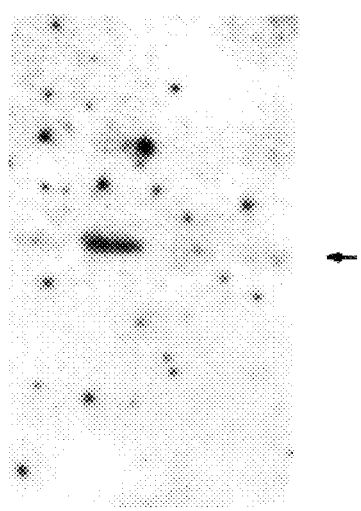
FIG. 9C
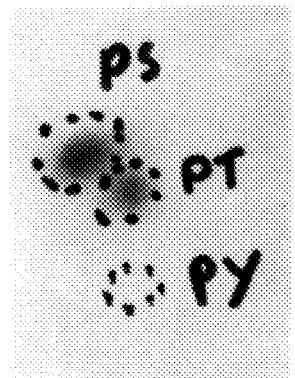

FIG. 10A
FIG. 10B
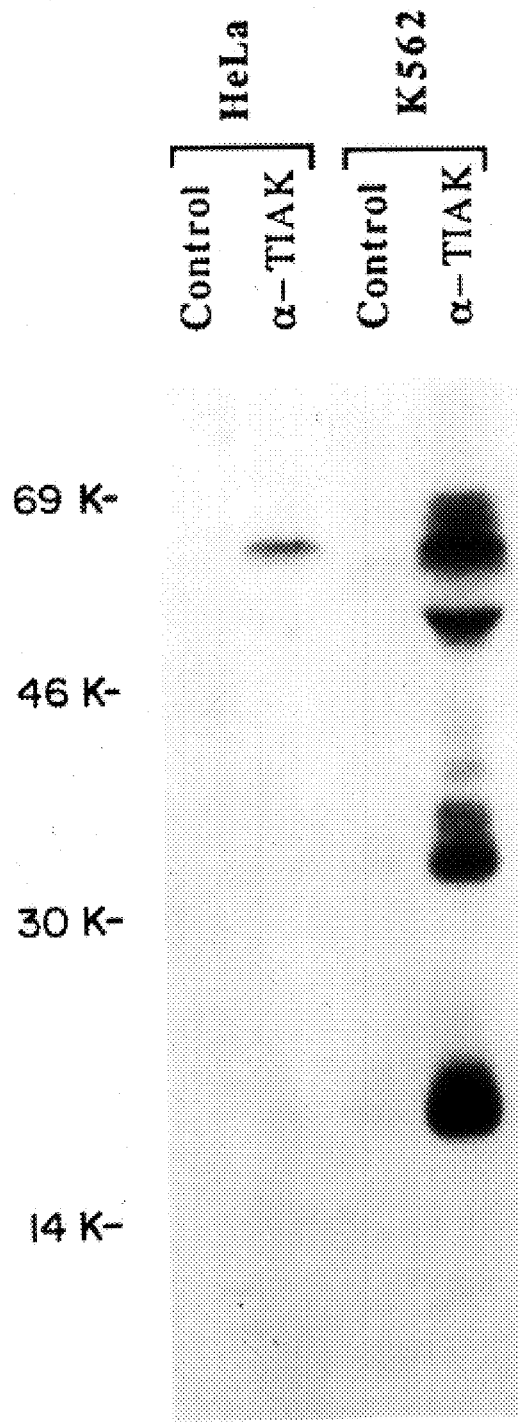
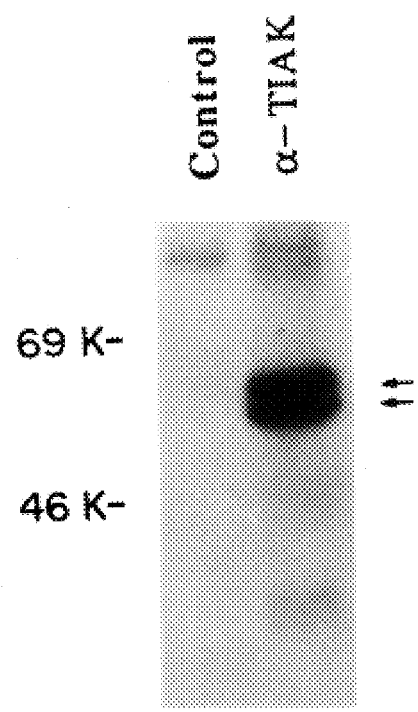
FIG. 10C
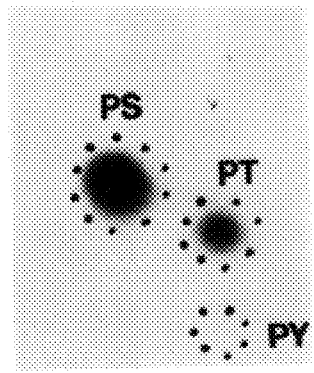

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1206 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 172..648

(xi) SEQUENCE DESCRIPTION: SEQ ID NO:1:

```
CCACCAAACC CAAAAAAAGA GATCTGGAAT TCGGATCCTC GAGGCCACGA AGGCCGCGGG      60

CTCCGGAGGG AAGTCCCGAG ACAAAGGGAA GCGCCGCCGC CGCCGCCCCG CTCGGTCCTC     120

CACCTGTCCG CTACGCTCGC CGGGGCTGCG GCCGCCCGAG GGACTTTGAA C ATG TCG     177
                                                        Met Ser
                                                         1
```

```
GGG ATC GCC CTC AGC AGA CTC GCC CAG GAG AGG AAA GCA TGG AGG AAA      225
Gly Ile Ala Leu Ser Arg Leu Ala Gln Glu Arg Lys Ala Trp Arg Lys
            5                  10                  15

GAC CAC CCA TTT GGT TTC GTG GCT GTC CCA ACA AAA AAT CCC GAT GGC      273
Asp His Pro Phe Gly Phe Val Ala Val Pro Thr Lys Asn Pro Asp Gly
         20                  25                  30

ACG ATG AAC CTC ATG AAC TGG GAG TGC GCC ATT CCA GGA AAG AAA GGG      321
Thr Met Asn Leu Met Asn Trp Glu Cys Ala Ile Pro Gly Lys Lys Gly
 35                  40                  45                  50

ACT CCG TGG GAA GGA GGC TTG TTT AAA CTA CGG ATG CTT TTC AAA GAT      369
Thr Pro Trp Glu Gly Gly Leu Phe Lys Leu Arg Met Leu Phe Lys Asp
                 55                  60                  65

GAT TAT CCA TCT TCG CCA CCA AAA TGT AAA TTC GAA CCA CCA TTA TTT      417
Asp Tyr Pro Ser Ser Pro Pro Lys Cys Lys Phe Glu Pro Pro Leu Phe
             70                  75                  80

CAC CCG AAT GTG TAC CCT TCG GGG ACA GTG TGC CTG TCC ATC TTA GAG      465
His Pro Asn Val Tyr Pro Ser Gly Thr Val Cys Leu Ser Ile Leu Glu
         85                  90                  95

GAG GAC AAG GAC TGG AGG CCA GCC ATC ACA ATC AAA CAG ATC CTA TTA      513
Glu Asp Lys Asp Trp Arg Pro Ala Ile Thr Ile Lys Gln Ile Leu Leu
100                 105                 110

GGA ATA CAG GAA CTT CTA AAT GAA CCA AAT ATC CAA GAC CCA GCT CAA      561
Gly Ile Gln Glu Leu Leu Asn Glu Pro Asn Ile Gln Asp Pro Ala Gln
115                 120                 125                 130

GCA GAG GCC TAC ACG ATT TAC TGC CAA AAC AGA GTG GAG TAC GAG AAA      609
Ala Glu Ala Tyr Thr Ile Tyr Cys Gln Asn Arg Val Glu Tyr Glu Lys
                135                 140                 145

AGG GTC CGA GCA CAA GCC AAG AAG TTT GCG CCC TCA TAAGCAGCGA           655
Arg Val Arg Ala Gln Ala Lys Lys Phe Ala Pro Ser
            150                 155

CCTTGTGGCA TCGTCAGAAG GAAGGGATTG GTTTGGCAAG AACTTGTTTA CAACATAATC    715

TAAAGTTGCT CCATACATGA CTAGTCACCT GGGGGGGTTG GGCGGGCGCA TCTTCCATTG    775

CCGCCGCGGG TGTGCGTCTC GATTCGCTGA ATTGCCCGTT TCCATACAGG GTCTCTTCCT    835

TCGGTCTTTT GTATTTTTGA TTGTTATGTA AAACTCGCTT TTATTTTAAT ATTGATGTCA    895

GTATTTCAAC TGCTGTAAAA TTATAAACTT TTATACTTGG GTAAGTCCCC AGGCGAGGTT    955

CCTCGCTCTG GGATGCAGGC ATGCTTCTCA CGTGCAGCTG TCAACTTGGC CTCAGCTGGC   1015

TGTATGGAAA TGCACCCTCC CTCCTGCGCT CCTCTCTAGA ACCGGCTAGA ACCTGGGCTG   1075

TGCTGCTTTT GAGCCTCAGA CCCCAGGGCA GCATCTCGGT TCTGCGCCAC TTCCTTTGTG   1135

TTTATATGGC GTTTTGTCTG TGTTGCTGTT TAGAGTAAAT AAAACTGTTT ATATAAAAAA   1195

AAAAAAAAA A                                                         1206

(2) INFORMATION FOR SEQ ID NO:2:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gly Ile Ala Leu Ser Arg Leu Ala Gln Glu Arg Lys Ala Trp
  1               5                  10                  15

Arg Lys Asp His Pro Phe Gly Phe Val Ala Val Pro Thr Lys Asn Pro
                 20                  25                  30

Asp Gly Thr Met Asn Leu Met Asn Trp Glu Cys Ala Ile Pro Gly Lys
             35                  40                  45
```

```
Lys Gly Thr Pro Trp Glu Gly Gly Leu Phe Lys Leu Arg Met Leu Phe
     50                  55                  60

Lys Asp Asp Tyr Pro Ser Ser Pro Pro Lys Cys Lys Phe Glu Pro Pro
 65                  70                  75                  80

Leu Phe His Pro Asn Val Tyr Pro Ser Gly Thr Val Cys Leu Ser Ile
                 85                  90                  95

Leu Glu Glu Asp Lys Asp Trp Arg Pro Ala Ile Thr Ile Lys Gln Ile
                100                 105                 110

Leu Leu Gly Ile Gln Glu Leu Leu Asn Glu Pro Asn Ile Gln Asp Pro
            115                 120                 125

Ala Gln Ala Glu Ala Tyr Thr Ile Tyr Cys Gln Asn Arg Val Glu Tyr
    130                 135                 140

Glu Lys Arg Val Arg Ala Gln Ala Lys Lys Phe Ala Pro Ser
145                 150                 155
```

(2) INFORMATION FOR SEQ ID NO:3:

(i) SEQUENCE CHARACTERISTICS:
        (A) LENGTH: 1776 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 19..1668

(xi) SEQUENCE DESCRIPTION: SEQ ID NO:3:

```
GGC GGA CTC GGT GGC TAG CCG ATG AGG AGG CCG CGG GGG GAA CCC GGC        48
                            Pro Met Arg Arg Pro Arg Gly Glu Pro Gly
                              1               5                  10

CCC CGG GCC CCG AGA CCG ACT GAG GGA GCG ACC TGC GCA GGG CCC GGG        96
Pro Arg Ala Pro Arg Pro Thr Glu Gly Ala Thr Cys Ala Gly Pro Gly
                 15                  20                  25

GAG TCA TGG TCT CCA TCA CCC AAC TCC ATG CTT CGA GTC CTG CTC TCT       144
Glu Ser Trp Ser Pro Ser Pro Asn Ser Met Leu Arg Val Leu Leu Ser
             30                  35                  40

GCT CAG ACC TCC CCT GCT CGG CTG TCT GGC CTG CTG CTG ATC CCT CCA       192
Ala Gln Thr Ser Pro Ala Arg Leu Ser Gly Leu Leu Leu Ile Pro Pro
         45                  50                  55

GTA CAG CCC TGC TGT TTG GGG CCC AGC AAA TGG GGG GAC CGG CCT GTT       240
Val Gln Pro Cys Cys Leu Gly Pro Ser Lys Trp Gly Asp Arg Pro Val
     60                  65                  70

GGA GGA GGC CCC AGT GCA GGT CCT GTG CAA GGA CTG CAG CGG CTT CTG       288
Gly Gly Gly Pro Ser Ala Gly Pro Val Gln Gly Leu Gln Arg Leu Leu
 75                  80                  85                  90

GAA CAG GCG AAG AGC CCT GGG GAG CTG CTG CGC TGG CTG GGC CAG AAC       336
Glu Gln Ala Lys Ser Pro Gly Glu Leu Leu Arg Trp Leu Gly Gln Asn
                 95                 100                 105

CCC AGC AAG GTG CGC GCC CAC CAC TAC TCG GTG GCG CTT CGT CGT CTG       384
Pro Ser Lys Val Arg Ala His His Tyr Ser Val Ala Leu Arg Arg Leu
            110                 115                 120

GGC CAG CTC TTG GGG TCT CGG CCA CGG CCC CCT CCT GTG GAG CAG GTC       432
Gly Gln Leu Leu Gly Ser Arg Pro Arg Pro Pro Pro Val Glu Gln Val
        125                 130                 135

ACA CTG CAG GAC TTG AGT CAG CTC ATC ATC CGA AAC TGC CCC TCC TTT       480
Thr Leu Gln Asp Leu Ser Gln Leu Ile Ile Arg Asn Cys Pro Ser Phe
    140                 145                 150

GAC ATT CAC ACC ATC CAC GTG TGT CTG CAC CTT GCA GTC TTA CTT GGC       528
```

-continued

```
Asp Ile His Thr Ile His Val Cys Leu His Leu Ala Val Leu Leu Gly
155                 160                 165                 170

TTT CCA TCT GAT GGT CCC CTG GTG TGT GCC CTG GAA CAG GAG CGA AGG        576
Phe Pro Ser Asp Gly Pro Leu Val Cys Ala Leu Glu Gln Glu Arg Arg
            175                 180                 185

CTC CGC CTC CCT CCG AAG CCA CCT CCC CCT TTG CAG CCC CTT CTC CGA        624
Leu Arg Leu Pro Pro Lys Pro Pro Pro Pro Leu Gln Pro Leu Leu Arg
                190                 195                 200

GGT GGG CAA GGG TTG GAA GCT GCT CTA AGC TGC CCC CGT TTT CTG CGG        672
Gly Gly Gln Gly Leu Glu Ala Ala Leu Ser Cys Pro Arg Phe Leu Arg
                    205                 210                 215

TAT CCA CGG CAG CAT CTG ATC AGC AGC CTG GCA GAG GCA AGG CCA GAG        720
Tyr Pro Arg Gln His Leu Ile Ser Ser Leu Ala Glu Ala Arg Pro Glu
        220                 225                 230

GAA CTG ACT CCC CAC GTG ATG GTG CTC CTG GCC CAG CAC CTG GCC CGG        768
Glu Leu Thr Pro His Val Met Val Leu Leu Ala Gln His Leu Ala Arg
235                 240                 245                 250

CAC CGG TTG CGG GAG CCC CAG CTT CTG GAA GCC ATT GCC CAC TTC CTG        816
His Arg Leu Arg Glu Pro Gln Leu Leu Glu Ala Ile Ala His Phe Leu
            255                 260                 265

GTG GTT CAG GAA ACG CAA CTC AGC AGC AAG GTG GTA CAG AAG TTG GTC        864
Val Val Gln Glu Thr Gln Leu Ser Ser Lys Val Val Gln Lys Leu Val
                270                 275                 280

CTG CCC TTT GGG CGA CTG AAC TAC CTG CCC CTG GAA CAG CAG TTT ATG        912
Leu Pro Phe Gly Arg Leu Asn Tyr Leu Pro Leu Glu Gln Gln Phe Met
            285                 290                 295

CCC TGC CTT GAG AGG ATC CTG GCT CGG GAA GCA GGG GTG GCA CCC CTG        960
Pro Cys Leu Glu Arg Ile Leu Ala Arg Glu Ala Gly Val Ala Pro Leu
    300                 305                 310

GCT ACA GTC AAC ATC TTG ATG TCA CTG TGC CAA CTG CGG TGC CTG CCC       1008
Ala Thr Val Asn Ile Leu Met Ser Leu Cys Gln Leu Arg Cys Leu Pro
315                 320                 325                 330

TTC AGA GCC CTG CAC TTT GTT TTT TCC CCT GGC TTC ATC AAC TAC ATC       1056
Phe Arg Ala Leu His Phe Val Phe Ser Pro Gly Phe Ile Asn Tyr Ile
            335                 340                 345

AGT GGC ACC CCT CAT GCT CTG ATT GTG CGT CGC TAC CTC TCC CTG CTG       1104
Ser Gly Thr Pro His Ala Leu Ile Val Arg Arg Tyr Leu Ser Leu Leu
                350                 355                 360

GAC ACG GCC GTG GAG CTG GAG CTC CCA GGA TAC CGG GGT CCC GCC CTT       1152
Asp Thr Ala Val Glu Leu Glu Leu Pro Gly Tyr Arg Gly Pro Arg Leu
            365                 370                 375

CCC CGA AGG CAG CAA GTG CCC ATC TTT CCC CAG CCT CTC ATC ACC GAC       1200
Pro Arg Arg Gln Gln Val Pro Ile Phe Pro Gln Pro Leu Ile Thr Asp
        380                 385                 390

CGT GCC CGC TGC AAG TAC AGT CAC AAG GAC ATA GTA GCT GAG GGG TTG       1248
Arg Ala Arg Cys Lys Tyr Ser His Lys Asp Ile Val Ala Glu Gly Leu
395                 400                 405                 410

CGC CAG CTG CTG GGG GAG GAG AAA TAC CGC CAG GAC CTG ACT GTG CCT       1296
Arg Gln Leu Leu Gly Glu Glu Lys Tyr Arg Gln Asp Leu Thr Val Pro
            415                 420                 425

CCA GGC TAC TGC ACA GAC TTC CTG CTG TGC GCC AGC AGC TCT GGT GCT       1344
Pro Gly Tyr Cys Thr Asp Phe Leu Leu Cys Ala Ser Ser Ser Gly Ala
        430                 435                 440

GTG CTT CCC GTG AGG ACC CAG GAC CCC TTC CTG CCA TAC CCA CCA AGG       1392
Val Leu Pro Val Arg Thr Gln Asp Pro Phe Leu Pro Tyr Pro Pro Arg
    445                 450                 455

TCC TGC CCA CAG GGC CAG GCT GCC TCT AGC GCC ACT ACT CGA GAC CCT       1440
Ser Cys Pro Gln Gly Gln Ala Ala Ser Ser Ala Thr Thr Arg Asp Pro
460                 465                 470

GCC CAG AGG GTG GTG CTG GTG TTG CGG GAA CGC TGG CAT TTC TGC CGG       1488
```

```
Ala Gln Arg Val Val Leu Val Leu Arg Glu Arg Trp His Phe Cys Arg
475                 480                 485                 490

GAC GGC CGG GTG CTG CTG GGC TCG AGG GCC CTG AGG GAG CGG CAC CTA       1536
Asp Gly Arg Val Leu Leu Gly Ser Arg Ala Leu Arg Glu Arg His Leu
                495                 500                 505

GGC CTG ATG GGC TAC CAG CTC CTG CCG CTA CCC TTC GAG GAA CTG GAG       1584
Gly Leu Met Gly Tyr Gln Leu Leu Pro Leu Pro Phe Glu Glu Leu Glu
                510                 515                 520

TCC CAG AGA GGC CTG CCC CAG CTC AAG AGC TAC CTG AGG CAG AAG CTC       1632
Ser Gln Arg Gly Leu Pro Gln Leu Lys Ser Tyr Leu Arg Gln Lys Leu
                525                 530                 535

CAA GCC CTG GGC CTG CGC TGG GGG CCT GAA GGG GGC TGA GGG GAT GAT       1680
Gln Ala Leu Gly Leu Arg Trp Gly Pro Glu Gly Gly
                540                 545                 550

GTG GGG TTC AGG ATG GCC CCC CCA TGG GGG GTG GAT GAT TTG CAC TTT       1728
GGT TCC CTG TGT TTT GAT TTC TCA TTA AAG TTC CTG GCC TTC AAA AAA       1776

(2) INFORMATION FOR SEQ ID NO:4:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:4:

Pro Met Arg Arg Pro Arg Gly Glu Pro Gly Pro Arg Ala Pro Arg Pro
1               5                   10                  15

Thr Glu Gly Ala Thr Cys Ala Gly Pro Gly Glu Ser Trp Ser Pro Ser
                20                  25                  30

Pro Asn Ser Met Leu Arg Val Leu Leu Ser Ala Gln Thr Ser Pro Ala
                35                  40                  45

Arg Leu Ser Gly Leu Leu Leu Ile Pro Pro Val Gln Pro Cys Cys Leu
            50                  55                  60

Gly Pro Ser Lys Trp Gly Asp Arg Pro Val Gly Gly Pro Ser Ala
65              70                  75                  80

Gly Pro Val Gln Gly Leu Gln Arg Leu Leu Glu Gln Ala Lys Ser Pro
                85                  90                  95

Gly Glu Leu Leu Arg Trp Leu Gly Gln Asn Pro Ser Lys Val Arg Ala
                100                 105                 110

His His Tyr Ser Val Ala Leu Arg Arg Leu Gly Gln Leu Leu Gly Ser
            115                 120                 125

Arg Pro Arg Pro Pro Val Glu Gln Val Thr Leu Gln Asp Leu Ser
130                 135                 140

Gln Leu Ile Ile Arg Asn Cys Pro Ser Phe Asp Ile His Thr Ile His
145                 150                 155                 160

Val Cys Leu His Leu Ala Val Leu Leu Gly Phe Pro Ser Asp Gly Pro
                165                 170                 175

Leu Val Cys Ala Leu Glu Gln Glu Arg Arg Leu Arg Leu Pro Pro Lys
                180                 185                 190

Pro Pro Pro Pro Leu Gln Pro Leu Leu Arg Gly Gly Gln Gly Leu Glu
                195                 200                 205

Ala Ala Leu Ser Cys Pro Arg Phe Leu Arg Tyr Pro Arg Gln His Leu
            210                 215                 220

Ile Ser Ser Leu Ala Glu Ala Arg Pro Glu Glu Leu Thr Pro His Val
225                 230                 235                 240

Met Val Leu Leu Ala Gln His Leu Ala Arg His Arg Leu Arg Glu Pro
```

245                 250                 255
Gln Leu Leu Glu Ala Ile Ala His Phe Leu Val Val Gln Glu Thr Gln
                260                 265                 270

Leu Ser Ser Lys Val Val Gln Lys Leu Val Leu Pro Phe Gly Arg Leu
            275                 280                 285

Asn Tyr Leu Pro Leu Glu Gln Gln Phe Met Pro Cys Leu Glu Arg Ile
        290                 295                 300

Leu Ala Arg Glu Ala Gly Val Ala Pro Leu Ala Thr Val Asn Ile Leu
305                 310                 315                 320

Met Ser Leu Cys Gln Leu Arg Cys Leu Pro Phe Arg Ala Leu His Phe
                325                 330                 335

Val Phe Ser Pro Gly Phe Ile Asn Tyr Ile Ser Gly Thr Pro His Ala
            340                 345                 350

Leu Ile Val Arg Arg Tyr Leu Ser Leu Leu Asp Thr Ala Val Glu Leu
        355                 360                 365

Glu Leu Pro Gly Tyr Arg Gly Pro Arg Leu Pro Arg Arg Gln Gln Val
    370                 375                 380

Pro Ile Phe Pro Gln Pro Leu Ile Thr Asp Arg Ala Arg Cys Lys Tyr
385                 390                 395                 400

Ser His Lys Asp Ile Val Ala Glu Gly Leu Arg Gln Leu Leu Gly Glu
                405                 410                 415

Glu Lys Tyr Arg Gln Asp Leu Thr Val Pro Pro Gly Tyr Cys Thr Asp
            420                 425                 430

Phe Leu Leu Cys Ala Ser Ser Gly Ala Val Leu Pro Val Arg Thr
        435                 440                 445

Gln Asp Pro Phe Leu Pro Tyr Pro Pro Arg Ser Cys Pro Gln Gly Gln
    450                 455                 460

Ala Ala Ser Ser Ala Thr Thr Arg Asp Pro Ala Gln Arg Val Val Leu
465                 470                 475                 480

Val Leu Arg Glu Arg Trp His Phe Cys Arg Asp Gly Arg Val Leu Leu
                485                 490                 495

Gly Ser Arg Ala Leu Arg Glu Arg His Leu Gly Leu Met Gly Tyr Gln
            500                 505                 510

Leu Leu Pro Leu Pro Phe Glu Glu Leu Glu Ser Gln Arg Gly Leu Pro
        515                 520                 525

Gln Leu Lys Ser Tyr Leu Arg Gln Lys Leu Gln Ala Leu Gly Leu Arg
    530                 535                 540

Trp Gly Pro Glu Gly Gly
545                 550

(2) INFORMATION FOR SEQ ID NO:5:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Ser Gly Ile Ala Leu Ser Arg Leu Ala Gln Glu Arg Lys Ala Trp
    1               5                   10                  15

Arg Lys Asp His Pro Phe Gly Phe Val Ala Val Pro Thr Lys Asn Pro
                20                  25                  30

Asp Gly Thr Met Asn Leu Met Asn Trp Glu Cys Ala Ile Pro Gly Lys
                35                  40                  45

```
Lys Gly Thr Pro Trp Glu Gly Gly Leu Phe Lys Leu Arg Met Leu Phe
 50              55                  60

Lys Asp Asp Tyr Pro Ser Ser Pro Pro Lys Cys Lys Phe Glu Pro Pro
 65              70                  75                  80

Leu Phe His Pro Asn Val Tyr Pro Ser Gly Thr Val Cys Leu Ser Ile
                 85                  90                  95

Leu Glu Glu Asp Lys Asp Trp Arg Pro Ala Ile Thr Ile Lys Gln Ile
                100                 105                 110

Leu Leu Cys Ile Gln Glu Leu Leu Asn Glu Pro Asn Ile Gln Asp Pro
                115                 120                 125

Ala Gln Ala Glu Ala Tyr Thr Ile Tyr Cys Gln Asn Arg Val Glu Tyr
130                 135                 140

Glu Lys Arg Val Arg Ala Gln Ala Lys Lys Phe Ala Pro Ser
145                 150                 155
```

(2) INFORMATION FOR SEQ ID NO:6:

(i) SEQUENCE CHARACTERISTICS:
        (A) LENGTH: 152 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Ser Thr Pro Ala Arg Arg Arg Leu Met Arg Asp Phe Lys Arg Leu
 1               5                  10                  15

Gln Glu Asp Pro Pro Val Gly Val Ser Gly Ala Pro Ser Glu Asn Asn
                 20                  25                  30

Ile Met Gln Trp Asn Ala Val Ile Phe Gly Pro Glu Gly Thr Pro Phe
                 35                  40                  45

Glu Asp Gly Thr Phe Lys Leu Leu Ile Glu Phe Ser Glu Glu Tyr Pro
 50                  55                  60

Asn Lys Pro Pro Thr Val Arg Phe Leu Ser Lys Met Phe His Pro Asn
 65                  70                  75                  80

Val Tyr Ala Asp Gly Ser Ile Cys Leu Asp Ile Leu Gln Asn Arg Trp
                 85                  90                  95

Ser Pro Thr Tyr Asp Val Ser Ser Ile Leu Thr Ser Ile Gln Ser Leu
                100                 105                 110

Leu Cys Glu Pro Asn Pro Asn Ser Pro Ala Asn Ser Gln Ala Ala Gln
                115                 120                 125

Leu Tyr Gln Glu Asn Lys Arg Glu Tyr Glu Lys Arg Val Ser Ala Ile
130                 135                 140

Val Glu Gln Ser Trp Asn Asp Ser
145                 150
```

(2) INFORMATION FOR SEQ ID NO:7:

(i) SEQUENCE CHARACTERISTICS:
        (A) LENGTH: 152 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Ser Thr Pro Ala Arg Arg Arg Leu Met Arg Asp Phe Lys Arg Leu
 1               5                  10                  15
```

```
    Gln Glu Asp Pro Pro Val Gly Val Ser Gly Ala Pro Ser Glu Asn Asn
                     20                  25                  30

Ile Met Gln Trp Met Ala Val Ile Phe Gly Pro Glu Gly Thr Pro Phe
                     35                  40                  45

Glu Asp Gly Thr Phe Lys Leu Val Ile Glu Phe Ser Glu Glu Tyr Pro
                     50                  55                  60

Asn Lys Pro Pro Thr Val Arg Phe Leu Ser Lys Met Phe His Pro Asn
    65                   70                  75                  80

Val Tyr Ala Asp Gly Ser Ile Cys Leu Asp Ile Leu Gln Asn Arg Trp
                         85                  90                  95

Ser Pro Thr Tyr Asp Val Ser Ser Ile Leu Thr Ser Ile Gln Ser Leu
                        100                 105                 110

Leu Asp Glu Pro Asn Pro Asn Ser Pro Ala Asn Ser Gln Ala Ala Gln
                        115                 120                 125

Leu Tyr Gln Glu Asn Lys Arg Glu Tyr Glu Lys Arg Val Ser Ala Ile
                        130                 135                 140

Val Glu Gln Ser Trp Asn Asp Ser
    145                 150

(2) INFORMATION FOR SEQ ID NO:8:

(i) SEQUENCE CHARACTERISTICS:
        (A) LENGTH: 152 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Ser Thr Pro Ala Arg Arg Arg Leu Met Arg Asp Phe Lys Arg Leu
    1               5                   10                  15

Gln Glu Asp Pro Pro Ala Gly Val Ser Gly Ala Pro Ser Glu Asn Asn
                     20                  25                  30

Ile Met Val Trp Asn Ala Val Ile Phe Gly Pro Glu Gly Thr Pro Phe
                     35                  40                  45

Gly Asp Gly Thr Phe Lys Leu Thr Ile Glu Phe Thr Glu Glu Tyr Pro
                     50                  55                  60

Asn Lys Pro Pro Thr Val Arg Phe Val Ser Lys Met Phe His Pro Asn
    65                   70                  75                  80

Val Tyr Ala Asp Gly Ser Ile Cys Leu Asp Ile Leu Gln Asn Arg Trp
                         85                  90                  95

Ser Pro Thr Tyr Asp Val Ser Ser Ile Leu Thr Ser Ile Gln Ser Leu
                        100                 105                 110

Leu Asp Glu Pro Asn Pro Asn Ser Pro Ala Asn Ser Gln Ala Ala Gln
                        115                 120                 125

Leu Tyr Gln Glu Asn Lys Arg Glu Tyr Glu Lys Arg Val Ser Ala Ile
                        130                 135                 140

Val Glu Gln Ser Trp Arg Asp Cys
    145                 150

(2) INFORMATION FOR SEQ ID NO:9:

(i) SEQUENCE CHARACTERISTICS:
        (A) LENGTH: 151 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:9:

Met Ser Thr Pro Ala Arg Arg Arg Leu Met Arg Asp Phe Lys Arg Leu
1               5                   10                  15

Gln Glu Asp Pro Pro Thr Gly Val Ser Gly Ala Pro Thr Asp Asn Asn
            20                  25                  30

Ile Met Ile Trp Asn Ala Val Ile Phe Gly Pro His Asp Thr Pro Phe
        35                  40                  45

Glu Asp Gly Thr Phe Lys Leu Thr Ile Glu Phe Thr Glu Glu Tyr Pro
    50                  55                  60

Asn Lys Pro Pro Thr Val Arg Phe Val Ser Lys Val Phe His Pro Asn
65                  70                  75                  80

Val Tyr Ala Asp Gly Gly Ile Cys Leu Asp Ile Leu Gln Asn Arg Trp
                85                  90                  95

Ser Pro Arg Tyr Asp Val Ser Ala Ile Leu Thr Ser Ile Gln Ser Leu
            100                 105                 110

Leu Ser Asp Pro Asn Pro Asn Ser Pro Ala Asn Ser Thr Ala Ala Gln
            115                 120                 125

Leu Tyr Lys Glu Asn Arg Arg Glu Tyr Glu Lys Arg Val Lys Ala Cys
    130                 135                 140

Val Glu Gln Ser Phe Ile Asp
145                 150

(2) INFORMATION FOR SEQ ID NO:10:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Ser Thr Thr Ala Arg Arg Arg Leu Met Arg Asp Phe Lys Arg Met
1               5                   10                  15

Gln Gln Asp Pro Pro Ala Gly Val Ser Ala Ser Pro Val Ser Asp Asn
            20                  25                  30

Val Met Leu Trp Asn Ala Val Ile Ile Gly Pro Ala Asp Thr Pro Phe
        35                  40                  45

Glu Asp Gly Thr Phe Lys Leu Val Leu Ser Phe Asp Glu Gln Tyr Pro
    50                  55                  60

Asn Lys Pro Pro Leu Val Lys Phe Val Ser Thr Met Phe His Pro Asn
65                  70                  75                  80

Val Tyr Ala Asn Gly Glu Leu Cys Leu Asp Ile Leu Gln Asn Arg Trp
                85                  90                  95

Ser Pro Thr Tyr Asp Val Ala Ala Ile Leu Thr Ser Ile Gln Ser Leu
            100                 105                 110

Leu Asn Asp Pro Asn Asn Ala Ser Pro Ala Asn Ala Glu Ala Ala Gln
            115                 120                 125

Leu His Arg Glu Asn Lys Lys Glu Tyr Val Arg Arg Val Arg Lys Thr
    130                 135                 140

Val Glu Asp Ser Trp Glu Ser
145                 150

(2) INFORMATION FOR SEQ ID NO:11:

(i) SEQUENCE CHARACTERISTICS:
    (A) LENGTH: 172 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:11:

Met Ser Thr Pro Ala Arg Arg Leu Met Arg Asp Arg Lys Arg Met
 1               5                  10                  15

Lys Glu Asp Ala Pro Pro Gly Val Ser Ala Ser Pro Leu Pro Asp Asn
            20                  25                  30

Val Met Val Trp Asn Ala Met Ile Ile Gly Pro Ala Asp Thr Pro Tyr
            35                  40                  45

Glu Asp Gly Thr Phe Arg Leu Leu Leu Glu Phe Asp Glu Tyr Pro
 50                  55                  60

Asn Lys Pro Pro His Val Lys Phe Leu Ser Glu Met Phe His Pro Asn
 65                  70                  75                  80

Val Tyr Ala Asn Gly Glu Ile Cys Leu Asp Ile Leu Gln Asn Arg Trp
                85                  90                  95

Thr Pro Thr Tyr Asp Val Ala Ser Ile Leu Thr Ser Ile Gln Ser Leu
                100                 105                 110

Phe Asn Asp Pro Asn Pro Ala Ser Pro Ala Asn Val Glu Ala Ala Thr
                115                 120                 125

Leu Phe Lys Asp His Lys Ser Gln Tyr Val Lys Arg Val Lys Glu Thr
130                 135                 140

Val Glu Lys Ser Trp Glu Asp Met Asp Asp Met Asp Asp Asp Asp
145                 150                 155                 160

Asp Asp Asp Asp Asp Asp Asp Asp Glu Ala Asp
                165                 170

(2) INFORMATION FOR SEQ ID NO:12:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AAGTCGTCG                                                                 9

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GCAGCCATTG                                                                10

(2) INFORMATION FOR SEQ ID NO:14:

(i) SEQUENCE CHARACTERISTICS:
        (A) LENGTH: 39 base pairs
        (B) TYPE: nucleic acid
        (C) STRANDEDNESS: double (D) TOPOLOGY: linear (ii) MOLECULE TYPE: DNA (genomic)

(ix) FEATURE:
         (A) NAME/KEY: CDS
         (B) LOCATION: 1..39

(xi) SEQUENCE DESCRIPTION: SEQ ID NO:14:

```
GGT ACC GTC GAC GCC GGC AAG CTT GCT GGA TCC TGT ACC              39
Gly Thr Val Asp Ala Gly Lys Leu Ala Gly Ser Cys Thr
 1               5                  10
```

(2) INFORMATION FOR SEQ ID NO:15:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:15:

```
Gly Thr Val Asp Ala Gly Lys Leu Ala Gly Ser Cys Thr
 1               5                  10
```

(2) INFORMATION FOR SEQ ID NO:16:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:16:

```
Pro Ser Lys Trp Gly Asp Arg Pro Val Gly Gly Pro Ser Ala Gly
 1               5                  10                  15

Pro Val Gln Gly Leu Gln Arg Leu Leu Gln Ala Lys Ser Pro Gly Glu
                20                  25                  30

Leu Leu Arg Trp Leu Gly Arg Asn Pro Ser Lys Val Arg Ala His His
                35                  40                  45

Tyr Ser Val Ala Leu Arg Arg Leu Gly Gln Leu Leu Gly Ser Arg Pro
 50                  55                  60

Arg Pro Pro Pro Val Glu Gln Val Thr Leu Gln Asp Leu Ser Gln Leu
 65                  70                  75                  80

Ile Ile Arg Asn Cys Pro Ser Phe Asp Ile His Thr Ile His Val Cys
                85                  90                  95

Leu His Leu Ala Val Leu Leu Gly Phe Pro Ser Asp Gly Pro Leu Val
                100                 105                 110

Cys Ala Leu Glu Gln Glu Arg Arg Leu Arg Leu Pro Pro Lys Pro Pro
                115                 120                 125

Pro Pro Leu Gln Pro Leu Leu Arg Gly Gly Gln Gly Leu Glu Ala Ala
                130                 135                 140

Leu Ser Cys Pro Arg Phe Leu Arg Tyr Pro Arg Gln His Leu Ile Ser
145                 150                 155                 160

Ser Leu Ala Glu Ala Arg Pro Glu Glu Leu Thr Pro His Val Met Val
                165                 170                 175

Leu Leu Ala Gln His Leu Ala Arg His Arg Leu Arg Glu Pro Gln Leu
                180                 185                 190

Leu Glu Ala Ile Ala His Phe Leu Val Val Gln Glu Thr Gln Leu Ser
                195                 200                 205
```

```
            Ser  Lys  Val  Val  Gln  Lys  Leu  Val  Leu  Pro  Phe  Gly  Arg  Leu  Asn  Tyr
                 210                 215                 220

Leu  Pro  Leu  Glu  Gln  Gln  Phe  Met  Pro  Cys  Leu  Glu  Arg  Ile  Leu  Ala
            225                 230                 235                 240

Arg  Glu  Ala  Gly  Val  Ala  Pro  Leu  Ala  Thr  Val  Asn  Ile  Leu  Met  Ser
                           245                 250                 255

Leu  Cys  Gln  Leu  Arg  Cys  Leu  Pro  Phe  Arg  Ala  Leu  His  Phe  Val  His
                      260                 265                 270

Ser  Pro  Gly  Phe  Ile  Asn  Tyr  Ile  Ser  Gly  Thr  Pro  His  Ala  Leu  Ile
                 275                 280                 285

Val  Arg  Arg  Thr  Leu  Ser  Leu  Leu  Asp  Thr  Ala  Val  Glu  Leu  Glu  Leu
                 290                 295                 300

Pro  Gly  Tyr  Arg  Gly  Pro  Arg  Leu  Pro  Arg  Arg  Gln  Gln  Val  Pro  Ile
            305                 310                 315                 320

Phe  Pro  Gln  Pro  Leu  Ile  Thr  Asp  Arg  Ala  Arg  Cys  Lys  Tyr  Ser  His
                           325                 330                 335

Lys  Asp  Ile  Val  Ala  Glu  Gly  Leu  Arg  Gln  Leu  Leu  Gly  Glu  Glu  Lys
                      340                 345                 350

Tyr  Arg  Gln  Asp  Leu  Thr  Val  Pro  Gly  Tyr  Cys  Thr  Asp  Phe  Leu
                 355                 360                 365

Leu  Cys  Ala  Ser  Ser  Gly  Ala  Val  Leu  Pro  Val  Arg  Thr  Gln  Asp
                 370                 375                 380

Pro  Phe  Leu  Pro  Tyr  Pro  Pro  Arg  Ser  Cys  Pro  Gln  Gly  Gln  Ala  Ala
            385                 390                 395                 400

Ser  Ser  Ala  Thr  Thr  Arg  Asp  Pro  Ala  Gln  Arg  Val  Val  Leu  Val  Leu
                           405                 410                 415

Arg  Glu  Arg  Trp  His  Phe  Ser  Arg  Asp  Gly  Arg  Val  Leu  Leu
                           420                 425                 430

(2) INFORMATION FOR SEQ ID NO:17:

(i) SEQUENCE CHARACTERISTICS:
        (A) LENGTH: 382 amino acids
        (B) TYPE: amino acid
        (D) TOPOLOGY: linear (ii) MOLECULE TYPE: protein (xi) SEQUENCE DESCRIPTION: SEQ ID NO:17:

Val  Ala  Val  Thr  Asn  Ile  Gly  Ala  Gly  Ser  Asp  Gly  Gly  Thr  Ala  Val
            1                 5                   10                  15

Val  Ala  Phe  Gly  Gly  Thr  Pro  Arg  Arg  Gly  Gly  Glu  Gly  Asp  Pro  Val
                           20                  25                  30

Gly  Pro  Ala  Glu  Phe  Val  Ser  Asp  Asp  Arg  Ser  Ser  Asp  Ser  Asp  Ser
                      35                  40                  45

Asp  Asp  Ser  Glu  Asp  Thr  Asp  Ser  Glu  Thr  Ile  Ser  His  Ala  Ser  Ser
                 50                  55                  60

Asp  Val  Ser  Gly  Gly  Ala  Thr  Tyr  Asp  Asp  Ala  Leu  Asp  Ser  Asp  Ser
            65                  70                  75                  80

Ser  Ser  Asp  Asp  Ser  Leu  Gln  Ile  Asp  Gly  Pro  Val  Cys  Arg  Pro  Trp
                           85                  90                  95

Ser  Asn  Asp  Thr  Ala  Pro  Leu  Asp  Val  Cys  Pro  Gly  Thr  Pro  Gly  Pro
                      100                 105                 110

Gly  Ala  Asp  Ala  Gly  Gly  Pro  Ser  Ala  Val  Asp  Pro  His  Ala  Pro  Thr
                 115                 120                 125

Pro  Glu  Ala  Gly  Ala  Gly  Leu  Ala  Ala  Asp  Pro  Ala  Val  Ala  Arg  Asp
            130                 135                 140
```

-continued

```
Asp Ala Glu Gly Leu Ser Asp Pro Arg Pro Arg Leu Gly Thr Gly Thr
145                 150                 155                 160

Ala Tyr Pro Val Pro Leu Glu Leu Thr Pro Glu Asn Ala Glu Ala Val
            165                 170                 175

Ala Arg Phe Leu Gly Asp Ala Val Asn Arg Glu Pro Ala Leu Met Leu
        180                 185                 190

Glu Tyr Phe Cys Arg Cys Ala Arg Glu Glu Thr Lys Arg Val Pro Pro
    195                 200                 205

Arg Thr Phe Gly Ser Pro Pro Arg Leu Thr Glu Asp Asp Phe Gly Leu
210                 215                 220

Leu Asn Tyr Ala Leu Val Glu Met Gln Arg Leu Cys Leu Asp Val Pro
225                 230                 235                 240

Pro Val Pro Pro Asn Ala Tyr Met Pro Tyr Tyr Leu Arg Glu Tyr Val
                245                 250                 255

Thr Arg Leu Val Asn Gly Phe Lys Pro Leu Val Ser Arg Ser Ala Arg
            260                 265                 270

Leu Tyr Arg Ile Leu Gly Val Leu Val His Leu Arg Ile Arg Thr Arg
        275                 280                 285

Glu Ala Ser Phe Glu Glu Trp Leu Arg Ser Lys Glu Val Ala Leu Asp
290                 295                 300

Phe Gly Leu Thr Glu Arg Leu Arg Glu His Glu Ala Gln Leu Val Ile
305                 310                 315                 320

Leu Ala Gln Ala Leu Asp His Tyr Asp Cys Leu Ile His Ser Thr Pro
                325                 330                 335

His Thr Leu Val Glu Arg Gly Leu Gln Ser Ala Leu Lys Tyr Glu Glu
            340                 345                 350

Phe Tyr Leu Lys Arg Phe Gly Gly His Tyr Met Glu Ser Val Phe Gln
        355                 360                 365

Met Tyr Thr Arg Ile Ala Gly Phe Leu Ala Cys Arg Ala Thr
370                 375                 380
```

(2) INFORMATION FOR SEQ ID NO:18:

(i) SEQUENCE CHARACTERISTICS:
        (A) LENGTH: 395 amino acids
        (B) TYPE: amino acid
        (D) TOPOLOGY: linear (ii) MOLECULE TYPE: protein (xi) SEQUENCE DESCRIPTION: SEQ ID NO:18:

```
Phe Val Ala Ile Ser Asn Val Ala Ala Gly Gly Asn Gly Arg Thr Ala
1               5                   10                  15

Val Val Ala Leu Gly Gly Thr Ser Gly Ala Arg Gly Gly Ala Glu Lys
            20                  25                  30

Asp Val Gly Ala Ala Glu Ser Trp Ser Asp Gly Pro Ser Ser Asp Ser
        35                  40                  45

Glu Thr Glu Asp Ser Asp Ser Ser Asp Glu Asp Thr Gly Ser Gly Ser
    50                  55                  60

Glu Thr Leu Ser Arg Ser Ser Ile Trp Ala Ala Gly Ala Thr Asp
65                  70                  75                  80

Asp Asp Asp Ser Asp Ser Asp Ser Arg Ser Asp Asp Ser Val Gln Pro
                85                  90                  95

Asp Val Val Val Arg Arg Trp Ser Asp Gly Pro Ala Pro Val Ala
            100                 105                 110

Phe Pro Lys Pro Arg Arg Pro Gly Asp Ser Pro Gly Asn Pro Gly Leu
```

```
                         115                 120                 125
        Gly Ala Gly Thr Gly Pro Gly Ser Ala Thr Asp Pro Arg Ala Ser Ala
            130                 135                 140
        Asp Ser Asp Ser Ala Ala His Ala Ala Pro Gln Ala Asp Val Ala
        145                 150                 155                 160
        Pro Val Leu Asp Ser Gln Pro Thr Val Gly Thr Asp Pro Gly Tyr Pro
                            165                 170                 175
        Val Pro Leu Glu Leu Thr Pro Glu Asn Ala Glu Ala Val Ala Arg Phe
                        180                 185                 190
        Leu Gly Asp Ala Val Asp Arg Glu Pro Ala Leu Met Leu Glu Tyr Phe
                    195                 200                 205
        Cys Arg Cys Ala Arg Glu Glu Ser Lys Arg Val Pro Pro Arg Thr Phe
        210                 215                 220
        Gly Ser Ala Pro Arg Leu Thr Glu Asp Phe Gly Leu Leu Asn Thr
        225                 230                 235                 240
        Ala Leu Ala Glu Met Arg Arg Leu Cys Leu Asp Leu Pro Val Pro
                            245                 250                 255
        Pro Asn Ala Tyr Thr Pro Tyr His Leu Arg Glu Tyr Ala Thr Arg Leu
                        260                 265                 270
        Val Asn Gly Phe Lys Pro Leu Val Arg Arg Ser Ala Arg Leu Tyr Arg
                    275                 280                 285
        Ile Leu Gly Ile Leu Val His Leu Arg Ile Arg Thr Arg Glu Ala Ser
        290                 295                 300
        Phe Glu Glu Trp Met Arg Ser Lys Glu Val Asp Leu Asp Pro Gly Leu
        305                 310                 315                 320
        Thr Glu Arg Leu Arg Glu His Glu Ala Gln Leu Met Ile Leu Ala Gln
                            325                 330                 335
        Ala Leu Asn Pro Tyr Asp Cys Leu Ile His Ser Thr Pro Asn Thr Leu
                        340                 345                 350
        Val Glu Arg Gly Leu Gln Ser Ala Leu Lys Tyr Glu His Tyr Leu
                    355                 360                 365
        Lys Arg His Gly Gly His Tyr Met Glu Ser Val His Gln Met Tyr Thr
        370                 375                 380
        Arg Ile Ala Gly Pro Leu Ala Cys Arg Ala Thr
        385                 390                 395

(2) INFORMATION FOR SEQ ID NO:19:

(i) SEQUENCE CHARACTERISTICS:
        (A) LENGTH: 282 amino acids
        (B) TYPE: amino acid
        (D) TOPOLOGY: linear (ii) MOLECULE TYPE: protein (xi) SEQUENCE DESCRIPTION: SEQ ID NO:19:

Met Glu Asn Tyr Gln Lys Val Glu Lys Ile Gly Glu Gly Thr Tyr Gly
1               5                   10                  15
Val Val Tyr Lys Ala Arg His Lys Leu Ser Gly Arg Ile Val Ala Met
                20                  25                  30
Lys Lys Ile Arg Leu Glu Asp Glu Ser Glu Gly Val Pro Ser Thr Ala
            35                  40                  45
Ile Arg Glu Ile Ser Leu Leu Lys Glu Val Asn Asp Glu Asn Asn Arg
        50                  55                  60
Ser Asn Cys Val Arg Leu Leu Asp Ile Leu His Ala Glu Ser Lys Leu
65                  70                  75                  80
```

```
Tyr Leu Val Phe Glu Phe Leu Asp Met Lys Leu Lys Tyr Met Asp
                85                  90                  95

Arg Ile Ser Phe Thr Gly Ala Thr Ser Leu Asp Pro Arg Leu Val Gln
           100                 105                 110

Lys Phe Thr Tyr Gln Leu Val Asn Gly Val Asn Phe Cys His Ser Arg
           115                 120                 125

Arg Ile Ile His Arg Asp Leu Lys Pro Gln Asn Leu Leu Ile Asp Lys
       130                 135                 140

Glu Gly Asn Leu Lys Leu Ala Asp Phe Gly Leu Ala Arg Ser Phe Gly
145                 150                 155                 160

Val Pro Leu Arg Asn Tyr Thr His Glu Ile Val Thr Leu Trp Tyr Arg
               165                 170                 175

Ala Pro Glu Val Leu Leu Gly Ser Arg His Tyr Ser Thr Gly Val Asp
           180                 185                 190

Ile Trp Ser Val Gly Cys Ile Phe Ala Glu Met Ile Arg Arg Ser Pro
           195                 200                 205

Leu Phe Pro Gly Asp Ser Glu Ile Asp Glu Ile Phe Lys Ile Phe Gln
           210                 215                 220

Val Leu Gly Thr Pro Asn Glu Glu Val Trp Pro Gly Val Thr Leu Leu
225                 230                 235                 240

Gln Asp Tyr Lys Ser Thr Phe Pro Arg Trp Lys Arg Met Asp Leu Tyr
               245                 250                 255

His Lys Val Val Pro Asn Gly Glu Glu Asp Ala Ile Glu Leu Leu Ser
               260                 265                 270

Ala Met Leu Val Tyr Asp Pro Ala His Arg
           275                 280

(2) INFORMATION FOR SEQ ID NO:20:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:20:

Met Glu Asn Phe Gln Lys Val Glu Lys Ile Gly Glu Gly Thr Tyr Gly
1                   5                  10                  15

Val Val Tyr Lys Ala Arg Asn Lys Leu Thr Gly Glu Val Val Ala Leu
               20                  25                  30

Lys Lys Ile Arg Leu Asp Thr Glu Thr Glu Gly Val Pro Ser Thr Ala
           35                  40                  45

Ile Arg Glu Ile Ser Leu Leu Lys Glu Leu Asn His Pro Asn Ile Val
       50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
           100                 105                 110

Gln Gly Leu Ala Arg Cys His Ser His Arg Val Leu His Arg Asp Leu
           115                 120                 125

Lys Pro Gln Asn Leu Leu Ile Asn Thr Glu Gly Ala Ile Lys Leu Ala
       130                 135                 140

Asp Phe Gly Leu Ala Arg Ala Phe Gly Val Pro Val Arg Thr Tyr Thr
145                 150                 155                 160
```

His Glu Val Val Thr Leu Trp Tyr Arg Ala Pro Glu Ile Leu Leu Gly
            165                 170                 175

Ser Lys Tyr Tyr Ser Thr Ala Val Lys Ile Trp Ser Leu Gly Cys Ile
            180                 185                 190

Phe Ala Glu Met Val Thr Arg Arg Ala Leu Phe Pro Gly Asp Ser Glu
            195                 200                 205

Ile Asp Gln Leu Phe Arg Ile Phe Arg Thr Leu Gly Thr Pro Asp Glu
210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
            245                 250                 255

Glu Asp Gly Arg Ser Leu Leu Ser Gln Met Leu His Tyr Asp Pro Asn
            260                 265                 270

Lys Arg (2) INFORMATION FOR SEQ ID NO:21:

(i) SEQUENCE CHARACTERISTICS:
        (A) LENGTH: 244 amino acids
        (B) TYPE: amino acid
        (D) TOPOLOGY: linear (ii) MOLECULE TYPE: protein (xi) SEQUENCE DESCRIPTION: SEQ ID NO:21:

Glu Ser Leu Arg Leu Glu Val Lys Leu Gly Gln Gly Cys Arg Gly Glu
1               5                   10                  15

Val Trp Met Gly Ile Trp Asn Gly Thr Thr Arg Val Ala Ile Lys Thr
            20                  25                  30

Leu Lys Pro Gly Thr Met Ser Pro Glu Ala Phe Leu Gln Glu Ala Gln
            35                  40                  45

Val Met Lys Lys Leu Arg His Glu Lys Leu Val Gln Leu Tyr Ala Val
50                  55                  60

Val Ser Glu Glu Pro Ile Tyr Ile Val Thr Glu Tyr Met Ser Lys Gly
65                  70                  75                  80

Ser Leu Leu Asp Phe Leu Lys Gly Glu Thr Gly Lys Tyr Leu Arg Leu
            85                  90                  95

Pro Gln Leu Val Asp Met Ala Ala Gln Ile Ala Ser Gly Met Ala Tyr
            100                 105                 110

Val Glu Arg Met Asn Tyr Val His Arg Asp Leu Arg Ala Ala Asn Ile
            115                 120                 125

Leu Val Gly Glu Asn Leu Val Cys Lys Val Ala Asp Phe Gly Leu Ala
130                 135                 140

Arg Leu Ile Glu Asp Asn Glu Tyr Thr Ala Arg Gln Gly Ala Lys Phe
145                 150                 155                 160

Pro Ile Lys Trp Thr Ala Pro Glu Ala Ala Leu Tyr Gly Arg Phe Thr
            165                 170                 175

Ile Lys Ser Asp Val Trp Ser Arg Gly Ile Leu Leu Thr Glu Leu Thr
            180                 185                 190

Thr Lys Gly Arg Val Pro Tyr Pro Gly Met Val Asn Arg Glu Val Leu
            195                 200                 205

Asp Gln Val Glu Arg Gly Tyr Arg Met Pro Cys Pro Pro Glu Pro Glu
210                 215                 220

```
Ser Leu His Asp Leu Met Cys Gln Cys Trp Arg Lys Glu Pro Glu Glu
225                 230                 235                 240

Arg Pro Thr Phe
```

1

TIA-1 BINDING PROTEINS AND ISOLATED COMPLEMENTARY DNA ENCODING THE SAME

This is a divisional of application Ser. No. 08/318,947 filed Oct. 6, 1994, now U.S. Pat. No. 5,788,245, which is a Continuation-in-Part of application Ser. No. 08/133,530, filed Oct. 7, 1993, now abandoned.

This invention was made with government support under Grant numbers AI 33600 and CA 53595 awarded by the National Institutes of Health. The government has certain rights in the invention.

FIELD OF THE INVENTION

The present invention relates to proteins that bind to TIA-1 and that are associated with lymphocytes. The present invention also relates to isolated cDNA encoding the binding proteins.

BACKGROUND OF THE INVENTION

Cytolytic lymphocytes (CTLs) possess cytoplasuic granules that are released in response to target cell recognition. CTL granules contain secretory proteins such as perforin and serine proteases, which are thought to contribute to the induction of target call death. Perforin has been shown to be directly cytolytic. In the presence of $Ca^{++}$, it inserts into the target cell plasma membrane where it aggregates to form osmotically active ion channels {Lichtenheld, M. G., et al, (1988), "Structure and function of human perforin", *Nature*, 335: 448–451; Hameed, A., et al, (1989), "Cytolysis by Ca-permable transmembrane channels. Pore formation causes extensive DNA-degradation and cell lysis", *J. Exp. Med.*, 169: 765–777}. The recent demonstration that transfection of perforin cDNA into rat basophilic leukemia (RBL) cells confers the ability to lyse erythrocytes via a regulated secretory mechanism supports a direct role for perforin in lymphocyte-mediated cytolysis {Shiver, J. W. and P. A. Henkart, (1991), "A noncytotoxic mast cell tumor line exhibits potent IgE-dependent cytotoxicity after transfection with the cytolysin/perforin gene", *Cell* 64: 1175–1181}. The inability of perforin-transfected RBL cells to efficiently lyse nucleated cells, however, suggests that additional granule components are required for optimal lymphocyte-mediated killing. That perforin is not the only cytolytic effector molecule is supported by the ability of natural killer (NK) cells and CTLs to kill some target cells in the absence of extracellular $Ca^{++}$, which is required for perforin activity {Tirosh, R. and G. Berke, (1985), "T Lymphocyte mediated cytolysis as an excitatory process of the target. I. Evidence that the target may be the site of calcium action", *Cell Immunol.*, 75: 113–123}. Furthermore, cytolytic lymphocytes that express little or no perforin (e.g., CD4+ CTL clones) have been shown to be potent cytolytic effector cells {Takayama, H., et al, (1991), "Antigen-specific directional target cell lysis by perforin-negative T lymphocyte clones", *Inter. Immunol.*, 3: 1149–1156}. The results imply that perforin-independent cytolytic effector mechanisms contribute to at least some forms of target cell killing.

In addition to perforin-mediated lysis, CTLs have been shown to induce in target cells a pathway of programmed cell death known as apoptosis {Russell, J. H. (1983), "Internal disintegration model of cytotoxic lymphocyte-induced target damage", *Immunol. Rev.*, 72: 97–118}. A convenient marker of this autolytic pathway is the fragmentation of target cell DNA into integer multiples of a 200 bp nucleosome-sized monomer {Wyllie, A. H., (1980), "Glucocorticoid-induced thymocyte apoptosis is associated with endogenous endonuclease activation", *Nature* 284: 555–556; Duke, R. C., et al, (1983), "Endogenous endonuclease-induced DNA fragmentation: an early event in cell-mediated cytolysis", *Proc. Natl. Acad. Sci.*, 80: 6361–6365}. The resulting "ladder" of DNA fragments is considered to be characteristic of this programmed suicide pathway. The observation that perforin induces cell lysis, but not DNA fragmentation {Duke, R. C., et al, (1989), "Purified perforin induces target cell lysis but not DNA fragmentation", *J. Exp. Med.*, 170: 1451–1456} suggests that other granule components are likely to be responsible for the induction of apoptotic cell death. The granzymes, a family of granule-associated serine proteases, are candidate perforin-independent cytolytic effector molecules {Pasternack, M. S. and H. N. Eisen, (1985), "A novel serine esterase expressed by cytotoxic T lymphocytes", *Nature*, 314: 743–745; Masson, D. and J. Tschopp, (1987), "A family of serine esterases in lytic granules of cytolytic T lymphocytes", *Cell* 49: 679–685}. Although purified granzymes are not directly cytotoxic, the ability of protease inhibitors to block lymphocyte-mediated cytolysis suggests that they play a role in target cell killing {Lavie, G., et al, (1985), "The mechanism of human NK cell mediated cytotoxicity. Mode of action of surface-associated proteases in the early stages of the lytic reaction", *J. Immunol.*, 135: 1470–1476; Rodgers, K. E., et al, (1988), "Inhibition of cytotoxic T lymphocyte and natural killer cell-mediated lysis by O,S,S-trimethyl phosphorodithioate is at an early post-recognition step", *J. Immunol.*, 140: 564–570}. The observation that granzyme A, the most abundant granule-associated serine protease, can induce DNA fragmentation in detergent permeabilized EL4 cells argues that these molecules might contribute to the induction of apoptosis in CTL targets {Hayes, M. P., et al, (1989), "Induction of target cell DNA release by the cytotoxic T lymphocyte granule protease granzyme A", *J. Exp. Med.*, 170: 933–946}. The further demonstration that the combination of granzymes and perforin can induce DNA fragmentation in unpermeabilized target cells suggests that perforin might be involved in the delivery of granzymes to target cells {Hayes, et al, supra, (1989); Shi, L., et al, (1992), "A natural killer cell granule protein that induces DNA fragmentation and apoptosis", *J. Exp. Med.*, 175: 553–566}. Finally, transfection of RBL cells with a combination of perforin and granzyme A confers the ability to induce DNA fragmentation in selected target cells {Shiver and Henkart, supra, (1991)}. Because the amount of DNA fragmentation induced by these cells is significantly less than that induced by CTLs, it is possible that additional granule-associated molecules are involved in the induction of apoptotic cell death.

Recently, another class of granule-associated proteins that are also able to induce DNA fragmentation in CTL target cells has been identified. TIA-1 is an RNA-binding protein that was initially identified by a monoclonal antibody (2G9) reactive with a 15 kD protein whose expression was restricted to CTLs and NK cells {Anderson, P., et al, (1990), "A monoclonal antibody reactive with a 15-kDa cytoplasmic granule-associated protein defines a subpopulation of CD8+ T lymphocytes", *J. Imunol.*, 144: 574–582}. Mitogenic activation induced the expression of immunoreactive isoforms of TIA-1 that migrated at 28 kD, 40 kD and 53 kD. Immunoselection of a λgt11 cDNA library using the monoclonal antibody reactive with TIA-1 identified two related cDNAs that encode p15-TIA-1 (1T4T8.9-5, 1.6 kb) and p40-TIA-1 (12G9.4, 2.2 kb) {Tian, Q., et al, (1991), "A polyadenylate binding protein localized to the granules of cytolytic lymphocytes induces DNA fragmentation in target cells", Cell, 67: 629–639}. Both TIA-1 isoforms were able to induce DNA fragmentation in permeabilized target cells, suggesting that they might be the granule-associated proteins responsible for the induction of apoptotic cell death in CTL target cells. Nothing is known about the molecular mechanisms by which TIA-1 triggers DNA fragmentation in target cells. Identification of cDNAs encoding TIA-1 binding proteins would be a first step in the molecular characterization of TIA-1 function. Further, characterization of the proteins would be useful to screen for drugs that induce apoptotic death in target cells.

SUMMARY OF THE INVENTION

Accordingly, one object of the present invention is to identify cDNAs encoding TIA-1 binding proteins.

These and other objects have been achieved by providing isolated cDNA comprising a sequence that encodes a polypeptide that binds TIA-1 in a double transformation.

In a preferred embodiment, the isolated cDNA sequence that encodes a polypeptide is SEQ ID NO:1 or SEQ ID NO:3.

The invention further provides isolated cDNA that hybridizes under stringent conditions to a nucleic acid probe comprising a six- to at least twenty-nucleotide segment having a sequence complementary to the six- to at least twenty-nucleotide segment of SEQ ID NO:1 or SEQ ID NO:3.

The invention even further provides isolated cDNA that hybridizes under low-stringency conditions to a nucleic acid probe comprising a sequence complementary to the coding sequence of SEQ ID NO:1 or SEQ ID NO:3.

The invention even further provides a purified nucleic acid that hybridizes under stringent conditions to a nucleic acid probe comprising a six- to at least a twenty-nucleotide segment of SEQ ID NO:1 or SEQ ID NO:3 or a segment having a complementary sequence to the six- to at least twenty-nucleotide segment.

The invention even further provides purified nucleic acid that hybridizes under low-stringency conditions to a nucleic acid probe comprising the coding sequence or a sequence complementary to the coding sequence of SEQ ID NO:1 or SEQ ID NO:3.

The invention even further provides a substantially pure polypeptide that binds TIA-1 in a double transformation.

In a preferred embodiment, the isolated polypeptide has an amino acid sequence that is SEQ ID NO:2 or SEQ ID NO:4.

The invention even further provides a substantially pure polypeptide that is immunologically reactive with monoclonal antibody 2B5 produced by a hybridoma designated ATCC #HB-11721.

BRIEF DESCRIPTION OF THE DRAWINGS

FIG. 2A is a schematic representation of the two-hybrid system used to identify cDNAs encoding TIA-1 binding proteins.

FIGS. 3A, 3B, 3C, 3D and 3E give the nucleotide sequence (SEQ ID NO:1) and deduced amino acid sequence (SEQ ID NO: 2) of TIABP1.

FIGS. 4A, 4B, 4C, 4D, 4E and 4F give the nucleotide sequence (SEQ ID NO:3) and deduced amino acid sequence (SEQ ID NO:4) of TIABP2.

FIG. 5 is a comparison of the deduced amino acid sequence of TIABP1 with the amino acid sequences of known E2-type ubiquitin conjugating enzymes. Amino acids common to all ubiquitin conjugating enzymes are depicted in bold type. In FIG. 5, HHR6B means human homolog of RAD6 {Koken M. H. M. et al., (1991) "Structural and Functional Conservation of Two Human Homologs of the Yeast DNA Repair Gene RAD6", Proc. natl. Acad. Sic., 88: 8865–8869}; Human E2 means E2-Type ubiquitin conjugating enzyme; HHR6A means Human homolog of RAD6 {Koken, M. H. M. et al, supra (1991)}; Dhr6 means Drosophila homolog of RAD6 {Koken M. et al, (1991), "Dhr6, a Drosophila homolog of the yeast DNA-repair gene RAD6", Proc. Natl. Acad. Sci., 88: 383203836}; rhp6 means RAD6 homolog in pombe {Reynolds P. et al, (1990), "The rhp6$^\pm$ gene of Schizosaccharomyces pombe: A Structural and Functional Homolog of the RAD6 Gene from the Distantly Related Yeast Saccharomyces cerevisiae", EMBO J., 9: 1423–1430}; and RAD6 means radiation mutant number 6 {Jentsch S. et al, (1987), "The Yeast DNA Repair Gene RAD6 Encodes a Ubiquitin-conjugating Enzymep", Nature, 329: 131–134}.

FIGS. 6A and 6B are schematic representations of the two-hybrid system used to screen for drugs inhibiting the interaction between TIA-1 and TIABP1.

FIG. 8 is a comparison of the deduced amino acid sequence of TIABP2 with several known protein kinases. Consensus sequences corresponding to the 10 signature motifs that define protein kinases are vindicated below the sequences. Consensus sequence V is omitted. Asterisks over the TIABP2 sequences indicate amino acids that are shared by TIABP2 and the HSV-2 kinase ICP10. Peptide inserts found in the TIABP2 sequence that are absent from the src sequence are indicated by lines labeled A through G.

FIGS. 9A, 9B, and 9C depict expression of recombinant TIABP2 in Cos cells.

Figure 1:
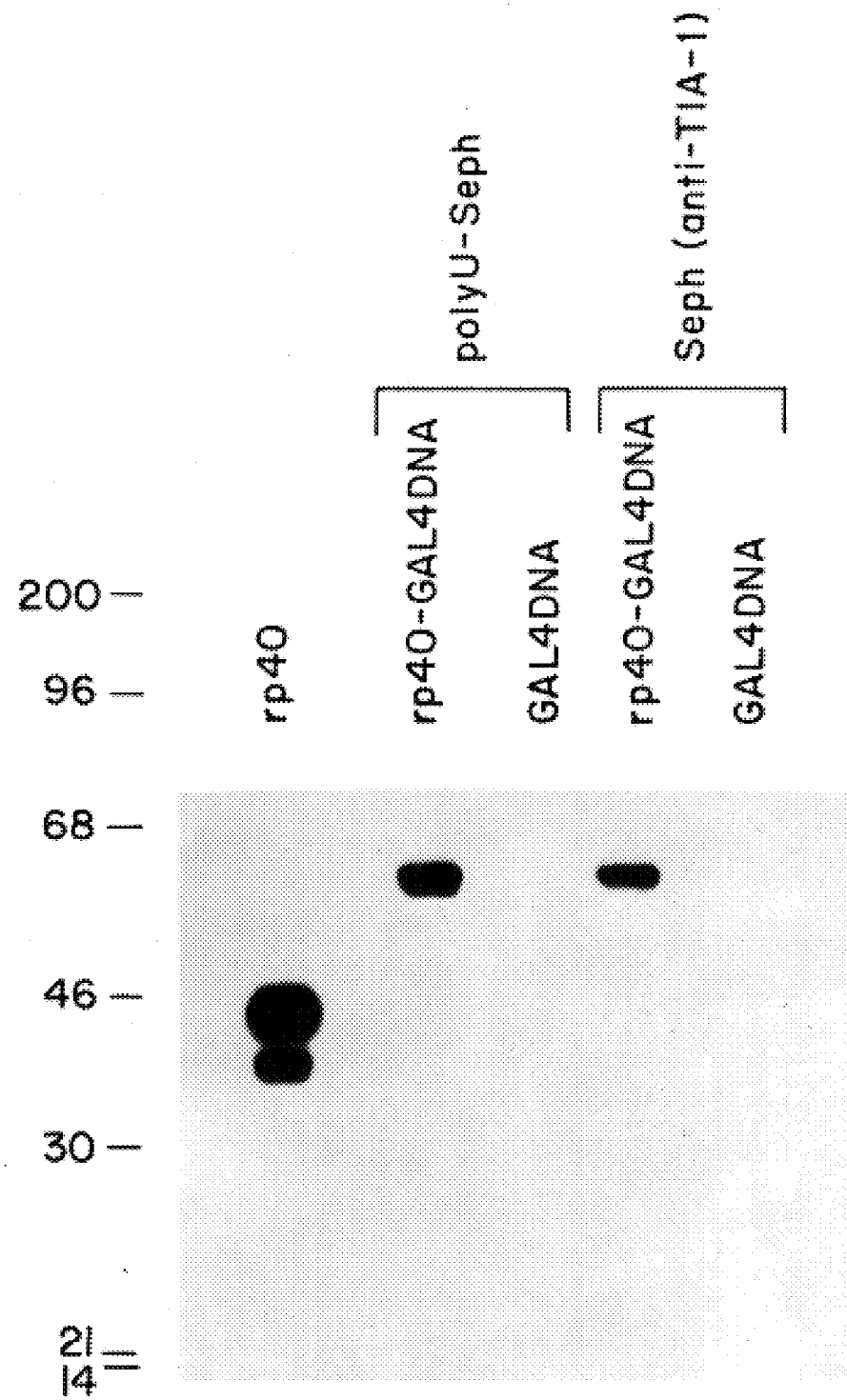
FIG. 1 represents an immunoblotting analysis of TIA-1 fusion proteins. Yeast strain GGY::171 was transformed with pMA424 encoding a fusion protein between the DNA binding domain of GAL4 and TIA-1 (rp40-GAL4DNA) or the GAL4 DNA binding domain alone (GAL4DNA). Yeast cell lysates were prepared using 2% TRITON X-100, 100 Mm NaCl, 100 mM Tris HCl, pH 8.0, 1 mM EDTA. Lysates were affinity precipitated using either poly(U)-agarose or SEPHAROSE immobilized anti-TIA-1. After separation on a 10% SDS polyacrylamide gel, and transfer to nitrocellulose, blots were probed with anti-TIA-1, and developed using the ECL method.

For FIG. 9A, Cos cells transformed with pMT2 (TIABP2) were lysed in NP-40 lysis buffer. Lysates were then immunoprecipitated with monoclonal antibodies reactive with the HA tag (anti-HA), TIABP2 (anti-2B5 designated anti-TIAK) or an isotype-matched control antibody. Immunoprecipitates were then subjected to an in vitro kinase assay {Parker, R., et al (1984), "Expression of v-src and chicken c-src in rat cells demonstrates qualitative differences between pp60 v-src and pp60 c-src", Cell, 37: 131}, separated on a 10% SDS polyacrylamide gel, and exposed for autoradiography. A prominent 65 kD protein which is the size expected of the hemagglutinin tagged TIABP2 molecule is identified in these autoradiograms (arrow). Lower molecular weight phosphoproteins might be proteolytic degradation products of the full length TIABP2 kinase. The relative migration of molecular-size markers is is shown at the left.

For FIG. 9B, Cos cell lysates prepared from cells transformed with pMT2 (HA-TIAPB2) (here designated Cos (HA-TIAK)) or the PMT vector alone (Cos (vector)), were immunoprecipitated with monoclonal antibodies reactive with the hemagglutinin tag (anti-HA) or with an isotype-matched control monoclonal antibody. Affinity precipitates were separated on a 10% SDS polyacrylamide gel, transferred to PVDF membranes, and then subjected to a renaturation procedure followed by the addition of $^{32}P\gamma$ ATP. After washing the filters, they were exposed for autoradiography. The autophosphorylated TIABP2 kinase was identified as a 65 kD phosphoprotein (arrow), confirming the intrinsic kinase activity of TIABP2. The autophosphorylated kinase was then excised from the PVDF filter and subjected to amino acid hydrolysis. Hydrolyzed amino acids were then separated on a two-dimensional electrophoresis, thin-layer chromatography apparatus (FIG. 9C). The relative migration of standards for phosphoserine (PS), phosphothreonine (PT) and phosphotyrosine (PY) are indicated. This analysis confirms that TIABP2 is a serine/threonine kinase.

FIGS. 10A, 10B, and 10C characterize natural TIABP2.

FIG. 10A is an immunoprecipitation of natural TIABP2 from lysates of HeLa cells and K562 cells. Immunoprecipitates were prepared using a monoclonal antibody reactive with TIABP2 (anti-2B5, here designated anti-TIAK) or with an isotype-matched control monoclonal antibody. Immunoprecipitates were subjected to the in vitro kinase assay prior to separation on a 10% SDS polyacrylamide gel. After transferring to nitrocellulose membranes, autoradiograms revealed a phosphorylated doublet centered around 65 kD which was specifically observed in immunoprecipitates prepared with antibodies reactive with TIABP2. In some cells (such as K562 shown in this figure), immunoprecipitates subjected to the in vitro kinase assay also included additional phosphoproteins migrating at 50 kD, 34 kD, and 21 kD. The identity of these candidate TIABP2 substrates is unknown. FIG. 10B shows that natural TIABP2 is a constitutively phosphorylated protein. In this experiment, Jurkat cells labeled with $^{32}P$-orthophosphate were lysed with NP-40 lysis buffer and immunoprecipitated with a monoclonal antibody reactive with TIABP2 (anti-2B5, here designated anti-TIAK) or with an isotype-matched control antibody. The monoclonal antibody reactive with TIABP2 specifically precipitated a phosphorylated doublet centered around 65 kD (arrows). When these phosphorylated bands were excised from the gel and subjected to amino acid hydrolysis, natural TIAK was found to be phosphorylated exclusively on serine and threonine residues (FIG. 10C).

Figure 11:
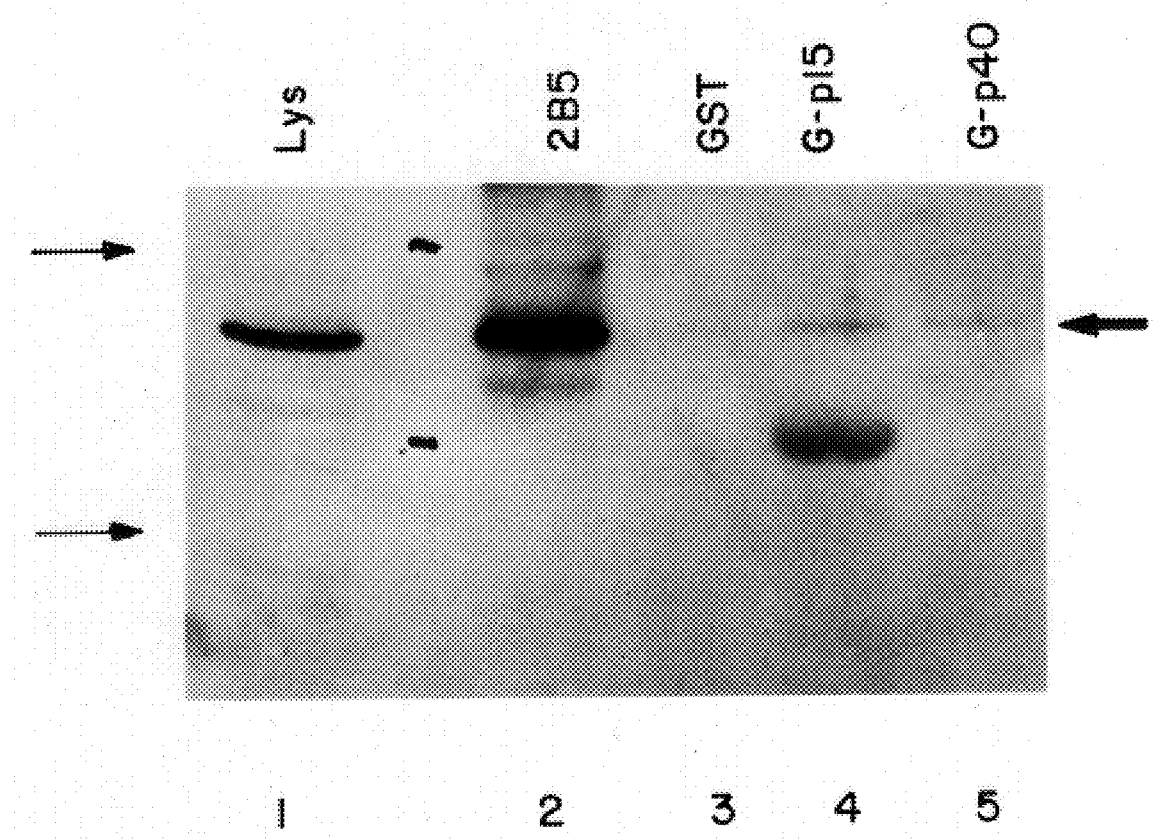

FIG. 11 shows the physical association between TIABP2 and TIA-1. Whole cell lysates prepared from Cos transformants expressing HA-TIABP2 were separated on a 10% SDS-polyacrylamide gel (lane 1), or affinity precipitated using mAb 2B5 (lane 2), immobilized GST (lane 3), GST-p15-TIA-1 (lane 4), or GST-p40-TIA-1 (lane 5). After transferring to nitrocellulose, the blot was probed with anti-2B5, a mAb reactive with TIABP2. The relative migration of molecular size markers is shown at the left.

Figure 12:
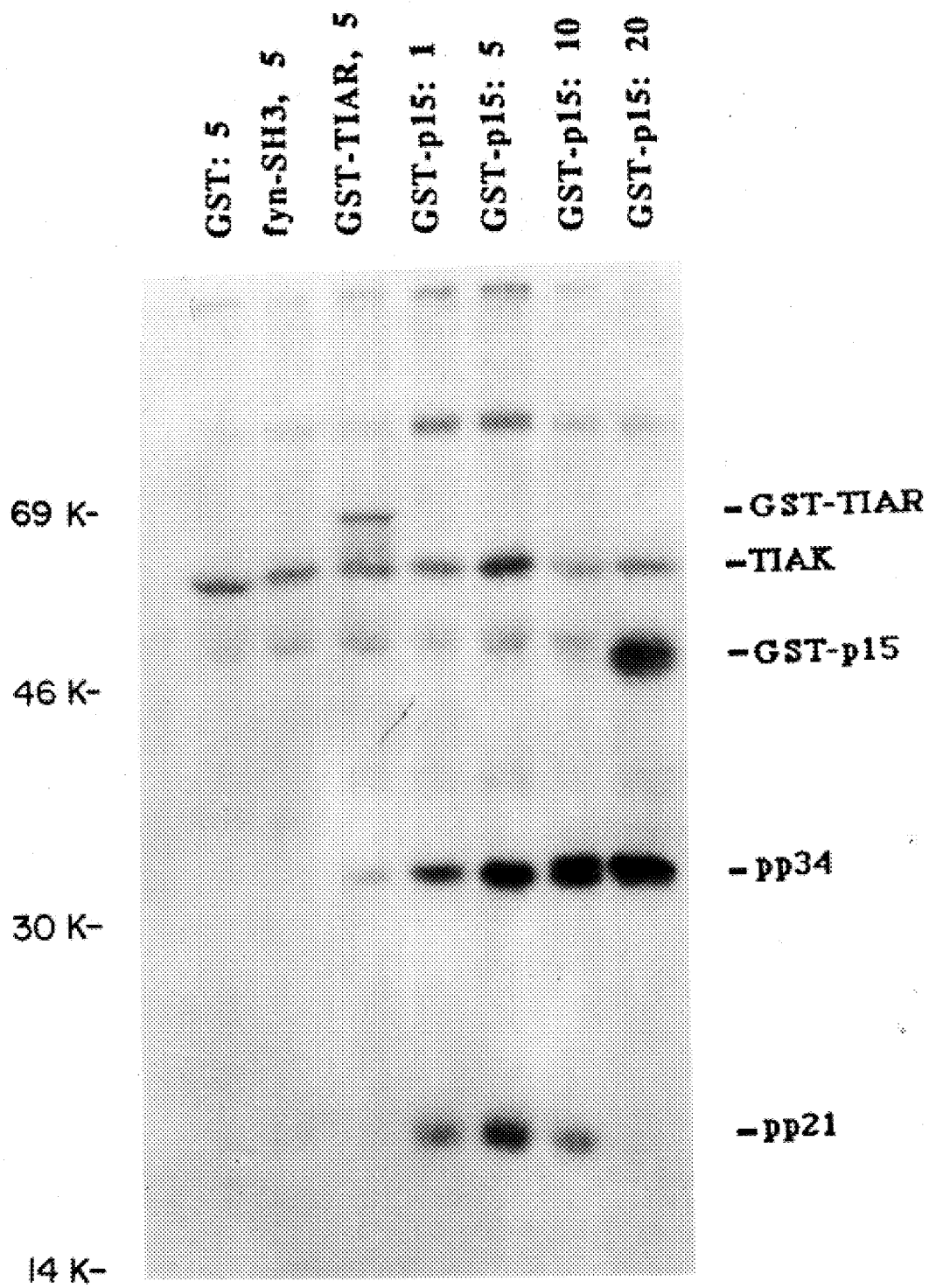

FIG. 12 shows the effects of p15-TIA-1 on the kinase activity of TIABP2. Lysates prepared from Cos cells transformed with TIABP2 were immunoprecipitated using anti-2B5, and subjected to the in vitro kinase assay in the presence of 5 μg/ml GST (lane 1), 5 μg/ml GST-fyn-SH3 (a fusion protein encoding GST at the amino terminus and the SH3 binding domain of the fyn kinase at the carboxyl terminus), (lane 2), 5 μg/ml GST-TIAR (a fusion protein between GST and the TIA-1 related protein TIAR), (lane 3), 1 μg/ml GST-p15-TIA-1 (lane 4), 5 μg/ml GST-p15-TIA-1 (lane 5), 10 μg/ml GST-p15-TIA-1 (lane 6), or 20 μg/ml GST-p15-TIA-1 (lane 7) as described in the Detailed Description of the Invention section. The relative migration of molecular-size markers is shown at the left. The relative migration of phosphorylated substrates is shown at the right.

DETAILED DESCRIPTION OF THE INVENTION

A family of cytotoxic granule-associated RNA-binding proteins (TIA-1 and TIAR) that appear to be involved in lymphocyte mediated cytolysis have been identified and are described in U.S. Pat. Nos. 5,079,343, 5,298,407, and 5,340,935 (all three of which are expressly incorporated herein by reference). The ability of purified recombinant TIA-1 and TIAR to induce DNA fragmentation in digitonin-permeabilized thymocytes suggests that these molecules activate an endogenous pathway of programmed cell death in CTL targeted cells. The molecular interactions by which TIA-1 and TIAR trigger programmed cell death are unknown. The present inventors have employed a genetic approach to identify molecular substrates for TIA-1 that might be involved in the programmed cell death pathway. Using the two hybrid system, the present inventors have isolated two distinct cDNAs encoding TIA-1 binding proteins and have designated them TIABP1 and TIABP2. TIABP1 and TIABP2 interact with the RNA-binding domain and the carboxy-terminal auxiliary domain of TIA-1, respectively. The deduced amino acid sequence of TIABP2 is related to the protein kinases and the deduced amino acid sequence of TIABP1 reveals it to be a member of a family of E2-type ubiquitin-conjugating enzymes. Because the ubiquitin pathway has been implicated in such diverse biologic processes as spermatogenesis, sporulation, DNA repair and programmed cell death, the interaction between TIA-1 and TIABP1 is expected to directly, or indirectly, trigger the programmed cell death pathway. Surprisingly, the present inventors found that p53, a tumor suppressor molecule that is also involved in triggering programmed cell death, also interacts with the ubiquitin conjugating enzyme TIABP1. Because the ubiquitin-mediated degradation of p53 is thought to be essential for malignant transformation induced by papilloma viruses, drugs that disrupt the interaction between TIABP1 and p53 are expected to have anti-tumor activity against HPV-induced human cancers.

The present invention includes an isolated cDNA comprising a sequence that encodes a polypeptide that binds TIA-1 in a double transformation. The isolated cDNA includes a sequence that encodes a polypeptide that binds the RNA binding domain and another sequence that binds the carboxy-terminal auxiliary domain of TIA-1.

The polypeptide that binds the carboxy-terminal auxiliary domain also is immunologically reactive with monoclonal antibody 2B5 produced by the hybridoma designated ATCC #HB-11721.

In a preferred embodiment, the isolated cDNA has a sequence, and the cDNA sequence encodes a polypeptide that is substantially identical to SEQ ID NO:1 or to SEQ ID NO:3.

Plasmids carrying the cDNA having SEQ ID NO:1 and SEQ ID NO:3 were deposited on Jul. 30, 1993, at the American Type Culture Collection (ATCC), 12301 Parklawn Drive, Rockville, Md. 20852 under the terms of the Budapest Treaty on the International Recognition of the Deposit of Microorganisms for the purposes of Patent Procedure. The plasmids were designated ATCC #69371 and ATCC #69372, respectively.

A hybridoma that produces a monoclonal antibody that reacts with TIABP2 and fragments of TIABP2 was deposited on Sep. 27, 1994; also at the ATCC under the terms of the Budapest Treaty. The hybridoma was designated ATCC #HB-11721.

The term "polypeptide" as used herein means a mature protein, precursors of the mature protein and fragments of either.

The phrase "isolated complementary DNA (cDNA)" as used herein is intended to denote a DNA molecule that is complementary to a naturally occurring mRNA encoding the TIA-1 binding proteins, and that has been engineered or synthesized so that the polypeptide-encoding sequence it includes is not flanked by the genes which, in the naturally-occurring genome of the organism from which such polypeptide-encoding sequence originated, normally flank such sequence.

The phrase "purified nucleic acid" as used herein means an RNA or DNA molecule that is substantially free of those other nucleic acid molecules with which it naturally associates within a cell: e.g., less than 30% of the purified nucleic acid preparation is made up of such contaminating naturally-occurring molecules. Either a purified nucleic acid or an isolated cDNA may be produced, for example, by cloning a fragment of genomic DNA, by creating a cDNA from a mRNA template, or by synthetically manufacturing a nucleic acid of the appropriate sequence.

The phrase "stringent conditions" as used herein to describe hybridization means the conditions described in Sambrook et al, Molecular Cloning: A Laboratory Manual; Cold Spring Harbor Laboratory, Cold Spring Harbor, N.Y., 1989. "Low-stringency conditions" as used herein to describe hybridization means the following: Prehybridization in 50% formamide, 5× SSC, 25 mM potassium phosphate buffer (pH 7.4), 5× Denhart's, and 50 $\mu$g/ml denatured salmon sperm DNA for 4–12 hours at 20° C.; hybridization for 12–24 hours at 20° C.; washing in 5× SSC containing 0.1% SDS, at 20° C.

The phrase "binds TIA-1 in a double transformation" as used herein means that the polypeptide encoded by the DNA binds in a double transformation, as described more fully in Example I herein, in which two fusion proteins are expressed, each fusion protein comprising a domain necessary for expression of a marker gene. One fusion protein comprises the polypeptide adjacent to one of the domains and the other fusion protein comprises TIA-1 adjacent to the other of the domains. When the polypeptide binds TIA-1, the two domains cooperate to express the marker gene.

The phrase "immunologically reactive" as used herein means that the antibody and antigen bind to each other (i.e., form an immune complex) with sufficient specificity to permit immunoassay of the antigen or antibody under standard conditions. The phrase does not necessarily exclude the possibility that the antibody binds other antigens: e.g., multimers of the antigen or related proteins as described below.

The term "TIA-1" as used herein includes within its scope naturally occurring TIA-1 as well as recombinant embodiments such as p40-TIA-1 and isoforms of p40-TIA-1.

The isoforms of p40-TIA-1 referred to above are those disclosed in the above mentioned U.S. Pat. Nos. 5,079,343, 5,298,407 and 5,340,935. The isoforms include the polypeptide designated as rp40-TIA-1 and the polypeptide designated as rp15-TIA-1, and these may have the specific amino acid sequences set forth in the referenced patents.

The term "substantially identical", when referring to a DNA sequence that encodes a polypeptide having a recited function means a DNA sequence that may be altered to substitute one codon coding for a specific amino acid for another codon coding for the same amino acid as well as a DNA sequence that has one or more nucleotide substitutions, deletions and/or insertions, but the encoded polypeptide retains its recited function. Thus, for example, a DNA base sequence substantially identical to a sequence that encodes a polypeptide that binds p40-TIA-1 or isoforms thereof could have nucleotide substitutions, deletions and/or insertions as long as the sequence encodes a polypeptide that binds TIA-1. Similarly, a DNA base sequence that encodes a polypeptide that has serine/threonine kinase activity could have nucleotide substitutions, deletions and/or insertions as long as the encoded polypeptide retains its serine/threonine kinase activity.

"Substantially identical" DNA sequences include allelic varients.

Appropriate substitutions, deletions and/or insertions can be made and tested by the skilled artisan. Specifically, cDNAs encoding TIABP1 or TIABP2 can be modified to specifically delete or insert one or more codons using site-directed mutagenesis {Foss K. and W. H. McClain, (1987), Gene, 59: 285–290}. By expressing these cDNAs as fusion proteins with, for example, the GAL4 activation domain, and producing double transformants as described in Example I, the resulting effect on the TIA-1 binding properties of the mutant can be determined.

DNA sequences that are "substantially identical" to the sequences coding for TIABP1 and TIABP2 and which therefore encode proteins that retain the ability to bind TIA-1, can be prepared in the following manner. By using a method known as linker scanning mutagenesis, a linker sequence recognized by both Kpn1 and Asp718 restriction enzymes (GGTACC:Kpn1 cuts between cytosine residues and Asp718 cuts between guanine residues) is inserted at 30 nucleotide intervals throughout the TIABP1 and the TIABP2 cDNAs. Individual linker sequences can be constructed using oligonucleotide mediated mutagenesis which is a common method in the art. The construction of these linker scanning mutants allows construction of cDNAs encoding 10 amino acid deletions throughout the coding sequence. In a similar manner, these mutants allow insertion of a random 10 amino acid sequence at any site within the coding region. This sequence can be produced using oligonucleotides encoding a random amino acid sequence which are flanked by Kpn1 Asp718.

```
G   T   V   D   A   G   K   L   A   G   S   G   T   amino acid sequence (SEQ ID NO: 15)

ggt acC GTC GAC GCC GGC AAG CTT GCT GGA TCC Tgt acc oligo 1              (SEQ ID NO: 14)

cCA TGG CAG CTG CGG CCG TTC GAA CGA CCT AGG CCA TGg oligo 2

KpnI    SalI    NaeI    HindIII     BamHI   Asp718  restriction sites
```

The sequence can be inserted into the coding sequence by cutting upstream linkers with Kpn1 and downstream linkers with Asp718. Each mutant can then be tested for its ability to bind specifically to the TIA-1 protein. In this way, substantially identical cDNAs that have deletions or insertions that do not affect the ability of their encoded proteins to interact with TIA-1 protein can be identified.

Also within the present invention is isolated cDNA that hybridizes under stringent conditions, as defined above, to a nucleic acid probe comprising a six-nucleotide segment (preferably at least 10 nucleotides, and more preferably at least 20 nucleotides) having a sequence complementary to a six- to at least twenty-nucleotide segment of SEQ ID NO:1 or SEQ ID NO:3.

The present invention also includes an isolated cDNA that hybridizes under low-stringency conditions, as defined above, to a nucleic acid probe comprising a sequence complementary to the coding sequence of SEQ ID NO:1 or SEQ ID NO:3.

In a further embodiment, the present invention includes a purified nucleic acid (DNA or RNA) that hybridizes under stringent conditions, as defined above, to a nucleic acid probe comprising a six-nucleotide segment (preferably at least 10 nucleotides, more preferably at least 20 nucleotides) of SEQ ID NO:1 or SEQ ID NO:3 or a segment having a complementary sequence to the six- to at least twenty-nucleotide segment.

The present invention further includes a purified nucleic acid (DNA or RNA) that hybridizes under low-stringency conditions, as defined above, to a nucleic acid probe comprising the coding sequence or a sequence complementary to the coding sequence of SEQ ID NO:1 or SEQ ID NO:3.

The substantially pure polypeptides referred to herein as binding to TIA-1 in a double transformation and/or as being immunologically reactive with monoclonal antibody 2B5 produced by hybridoma ATCC #HB-11721, are naturally occurring compounds, recombinantly produced compounds, or synthetically prepared compounds or fragments of the compounds. The genetically-engineered forms or those synthetically produced may differ from the protein defined by SEQ ID NOS:2 and 4 by one or more (but less than about 70%) of its amino acid residues (i.e., there should be about 30% amino acid identity), so long as they retain the recited function.

The phrase "amino acid sequence substantially identical to" means an amino acid sequence that differs from the recited sequence by one or more (but less than 70%) of its amino acid residues and retains the function of the referenced amino acid sequence as determined by routine experimentation.

I. Isolation of cDNA Clones Encoding TIA-1 Binding Proteins

The cDNA encoding p40-TIA-1 was cloned, by known methods, into the multilinker of the publicly available pMA424 vector to produce a fusion protein consisting of the GAL4 DNA binding domain (1–147) at the amino terminus and p40-TIA-1 at the carboxyl terminus. Transformation of yeast strain GGY::171 with this recombinant plasmid followed by selection on SC-His plates resulted in the efficient expression of the fusion protein as shown in FIG. 1. Because this fusion protein lacks the GAL4 activation domain, it is unable to induce β-galactosidase expression, which in GGY::171 is under control of the GAL4 promoter. The identification of cDNAs encoding TIA-1 binding proteins can then be accomplished by co-transforming GGY::171 cells with pMA424 (TIA-1) and clones from a cDNA library (e.g., B cell cDNA is cloned into the Xho I site of pSE1107) expressing fusion proteins consisting of the GAL4 activation domain (768–881) at the amino terminus and peptides encoded by individual cDNAs at the carboxyl terminus (FIG. 2A). Selection for double transformants expressing β-galactosidase (i.e., blue colonies on X-gal plates) identifies cDNAs encoding candidate TIA-1 binding proteins that juxtapose the GAL4 activation domain and the GAL4 DNA binding domain as a consequence of the TIA1:TIA-1-binding protein interaction. By screening the double transformants in this manner, β-galactosidase expressing colonies can be identified. Of these, those expressing a 1.2 kb insert and those expressing a 1.5 kb insert coding for the TIA-1 binding proteins (TIABP1 and TIABP2) of the present invention were isolated.

One colony induced the expression of significantly more β-galactosidase than the others, prompting its selection for further analysis. The pSE1107 plasmid isolated from this colony contained a 1.5 kb cDNA insert capable of encoding an amino acid peptide, designated TIABP2, fused to the GAL4 transactivation domain. Because truncation mutants of TIA-1 possessing only the three RNA binding domains (delta 207) did not induce β-galactosidase expression with TIABP2, it is likely that TIABP2 interacts with the carboxy-terminal protein interaction domain of TIA-1 (data not shown) as schematized in FIG. 2B. Interestingly, interaction of TIABP2 with TIAR {Kawakami, A. T., et al, (1992), "Identification and functional characterization of a TIA-1-related nucleolysin", *Proc. Natl. Acad. Sci. USA,* 89: 8681–8685}, a TIA-1 related RNA binding protein capable of triggering DNA fragmentation in permeabilized thymocytes, also induced β-galactosidase expression in the yeast two-hybrid system. TIABP2 did not, however, interact with another RRM-type RNA-binding protein, the human poly(A)-binding protein, nor did it interact with several control proteins including p53 and Rb, suggesting that its interaction with TIA-1 and TIAR is specific. The 1.5 kb insert encoding TIABP2 was used to screen a placental cDNA library by hybridization. This resulted in isolation of a 1.8 kb cDNA. Because the first methionine conforms to the consensus "Kozak" sequence {Kozak, M. 1984. Compilation and analysis of sequences upstream from the translational start site in eukaryotic mRNAS. *Nucl. Acids Res.* 12: 857}, it is likely to encode the initiating methionine. Northern blots probed with this 1.8 kb cDNA detected a widely expressed 1.8 kb mRNA (FIG. 7).

The nucleotide sequences (SEQ ID NO:1 and SEQ ID NO:3) and deduced amino acid sequences (SEQ ID NO:2 and SEQ ID NO:4) of TIABP1 and TIABP2 are shown in FIGS. 3 and 4, respectively.

Because truncation mutants of TIA-1 possessing only the three RNA binding domains (delta 207) induced β-galactosidase expression with TIABP1 but not with TIABP2, TIABP1 is believed to interact with the RNA binding domain of TIA-1. Further, the deduced amino acid sequence of TIABP1 was found to be structurally related to a family of E2 type ubiquitin activating enzymes (FIG. 5) found in the databases GenBank-76 and NBRF PIR-36.

TIABP1 and TIABP2 can be expressed in prokaryotic cells, preferably *E. coli,* and in eukaryotic cells by methods known in the art. Both TIABP1 and TIABP2 have been cloned into the pGEX vector and expressed as fusion proteins with glutathione-S-transferase. By transformation of *E. coli*, strain DH5, with these recombinant expression vectors, fusion peptides including TIABP1 and TIABP2 were purified. In addition, both TIABP1 and TIABP2 were cloned into the pMT2 vector and used to transform Cos cells in a transient assay. Both proteins were expressed in these cells as demonstrated by their reactivity with both polyclonal and monoclonal antibodies specific for each polypeptide.

II. Interaction between TIABP1 and p53

E2-type ubiquitin conjugating enzymes (UCE) transfer ubiquitin to the epsilon amino groups of lysine residues on selected substrates. Although the determinants of substrate specificity for individual UCEs are poorly understood, individual UCEs have the potential to ubiquitinate more than one substrate. Because of this, TIABP1 was screened for the ability to interact with molecular substrates that might, like TIA-1, be involved in cell cycle progression. As shown in the Table below, the tumor suppressor gene p53 was uniquely able to interact with TIABP1 to induce the expression of β-galactosidase in yeast transformants. Importantly, previously identified mutant forms of p53 that lacked tumor suppressor activity (i.e., 175, 273) induced significantly less β-galactosidase expression. In each case, fusion proteins were designed to exclude the transactivation domain of p53 (aa 1–73) to avoid its influence on the transcriptional activation of β-galactosidase.

TABLE

Expression of β-galactosidase in Yeast Double-transformants

| Fusion protein A (units) | Fusion protein B | β-gal |
|---|---|---|
| GAL4DNA:p53 | GAL4TA:TIABP2 | 0.45 |
| GAL4DNA:p40-TIA-1 | GAL4TA:TIABP2 | 142.86 |
| GAL4DNA:RB | GAL4TA:TIABP2 | 0.33 |
| GAL4DNA:RB | GAL4TA:TIABP1 | 0.36 |
| GAL4DNA:p53(W) | GAL4TA:TIABP1 | 84.79 |
| GAL4DNA:p53(273) | GAL4TA:TIABP1 | 60.59 |
| GAL4DNA:p53(175) | GAL4TA:TIABP1 | 62.50 |
| GAL4DNA:p40-TIA-1 | GAL4TA:TIABP1 | 40.21 |

The p53 gene product is thought to block cell cycle progression at the G1/S boundary. Its expression is therefore antiproliferative, and its inactivation appears to be required for the malignant transformation of a number of cell types. The ubiquitin-mediated degradation of p53 has been shown to be an important post-translational event in the regulation of p53 expression. In malignant transformation induced by papilloma viruses, inactivation of p53 requires the E6 viral protein, which enhances its ubiquitin-mediated degradation. Cervical carcinomas resulting from papilloma virus infection are characterized by their low levels of p53 expression. If TIABP1 is specifically involved in the ubiquitin-mediated degradation of p53, this interaction may be a critical step in malignant transformation.

III. Protein Kinase Activity of TIABP2

Comparison of the amino acid sequence of TIABP2 with sequences in the EMBL protein database revealed a weak similarity with a serine/threonine kinase encoded by herpes simplex viruses (HSV) 1 and 2 (FIG. 8). This observation led the inventors to compare the amino acid sequence of TIABP2 with signature sequences indicative of protein kinase activity (FIG. 8). Although TIABP2 does not encode all of the "invariant" consensus residues, its sequence is similar to that of the known kinases in each of 10 highly conserved regions (FIG. 8). TIABP2 is expressed in Cos cells as a fusion protein encoding an amino terminal hemaglutinin (HA) epitope tag. Immunoprecipitates prepared using anti-HA were subjected to the in vitro kinase assay and separated on a 10% SDS polyacrylamide gel. These immunoprecipitates contain the expected 65 kD HA-TIABP2 fusion protein (FIG. 9A, arrow) indicating that TIABP2 possesses intrinsic protein kinase activity. The protein kinase activity of TIABP2 was confirmed in the renaturation kinase assay shown in FIG. 9B. In this experiment, Cos cells transformed with the hemagglutinin tagged version of TIABP2 or with the vector alone were lysed with NP-40 lysis buffer and immunoprecipitated with antibodies reactive with the HA tag. Cos cells expressing HA-TIABP2 (here designated HA-TIAK) specifically included a 65 kD protein which was phosphorylated in this renaturation kinase assay (FIG. 9B, arrow). This assay confirms that the 65 kD phosphoprotein possesses intrinsic tyrosine kinase activity and that it is not a transphosphorylation product of an associated protein kinase. The amino acid specificity of the TIABP2 kinase was determined by analysis of hydrolytic digests of the autophosphorylated TIABP2 kinases shown in FIG. 9C. This analysis indicates that TIABP2 is a serine/threonine kinase.

IV. Characterization of Natural TIABP2

A monoclonal antibody reactive with recombinant TIABP2 (FIG. 10A), labeled anti-TIAK), but not an isotype-matched control antibody, precipitated a doublet centered around 65 kD from both HeLa and K562 lysates that were specifically labeled in the in vitro kinase assay. Immunoprecipitates prepared from K562 cell lysates also included additional phosphoproteins migrating at 50 kD, 34 kD, and 21 kD. Although the identity of these associated proteins is unknown, they are possible substrates for the kinase activity of TIABP2. Natural TIABP2 expressed in Jurkat cells was found to be a constitutively phosphorylated protein which migrated as a doublet centered around 65 kD (FIG. 10B, arrows). The constitutive phosphorylation of TIABP2 occurred exclusively on serine and threonine residues as shown in the phosphoamino acid analysis shown in FIG. 10C.

V. Physical Interaction between TIA-1 and TIABP2

Results obtained using the yeast two-hybrid system suggested a specific interaction between TIABP2 and the protein interaction domain of TIA-1. These results were confirmed by showing that TIABP2 contained in lysates from Cos transformants could be specifically co-precipitated by GST fusion proteins expressing the protein interaction domain of TIA-1. FIG. 11 shows that lysates prepared from Cos cells transformed with TIABP2 contain a 65 kD protein that is recognized by a monoclonal antibody reactive with TIABP2 (lane 1). Affinity precipitates prepared using glutathione beads coupled to GST did not contain the 65 kD recombinant TIABP2 protein (lane 2). Affinity precipitates prepared using glutathione beads coupled to either GST-p15-TIA-1 (lane 3) or GST-p40-TIA-1 (lane 4) included the 65 kD TIABP2 protein. This result is consistent with results obtained using the two hybrid system, and suggest that TIABP2 interacts with the carboxy terminal protein interaction domain of TIA-1.

VI. Regulation of TIABP2 by TIA-1

Cos cells transformed with a cDNA encoding TIABP2 were lysed with NP-40 lysis buffer and immunoprecipitated using anti-2B5. These immunoprecipitates were subjected to the in vitro kinase assay in the presence of GST-fusion proteins encoding either control peptides or p15-TIA-1 (FIG. 12). Each of these immunoprecipitates expressed a 65 kD phosphoprotein migrating in the position expected for TIABP2 (in FIG. 12 designated TIAK). In the presence of GST alone or a GST-fusion protein encoding the SH3 domain of the fyn tyrosine kinase, additional transphorylated substrates were not identified. However, in the presence of GST-fusion proteins encoding p15-TIA-1, the appearance of transphosphorylated substrates migrating at 34 kD and 21 kD were induced in a dose-dependent manner. The 21 kD phosphoprotein was not observed at the highest concentration of GST-p15-TIA-1 (20 µg/ml). At this concentration, the GST-p15-TIA-1 itself became a target for phosphorylation, suggesting that competition for phosphorylation of the two proteins might be responsible for this result. The autophosphorylation of TIABP2 was not changed in the presence or absence of GST-p15-TIA-1. These results suggest that TIA-1 can alter the ability of TIABP2 to transphosphorylate associated substrates.

VII. Use

The ability of TIA-1 to enhance the protein kinase activity of TIABP2 suggests that the activation of TIABP2 may be required for the induction of apoptotic cell death. Because the kinase activity of TIABP2 can be easily measured in vitro, it will be possible to screen for small drugs which either activate or inhibit the activity of this serine/threonine kinase. It will also be possible to screen for small drugs that disrupt the specific association between TIA-1 and TIABP2 that is likely to occur during CTL-mediated killing of target cells. Such drugs would be expected to have protective activity against inflammatory conditions in which TIA-1-mediated killing of target cells induced by cytotoxic T lymphocytes is important in the pathophysiology of disease. Examples of such diseases would include graft vs. host disease of the skin, renal allograft rejection, and all transplantation organ rejections.

TIA-1 is a cytotoxic granule-associated RNA binding protein that is a candidate toxin used by cytotoxic lymphocytes in the destruction of target cells. Although the molecular mechanisms responsible for the toxic effects of TIA-1 are unknown, the ability of purified recombinant TIA-1 to induce DNA fragmentation in permeabilized target cells suggests that this protein might induce apoptotic death in cells into which it is introduced. Target cell proteins that interact with TIA-1 are candidate substrates in a molecular cascade leading to target cell death. As such, cDNAs encoding TIABP1 and TIABP2 and the recombinant proteins that they encode, can be used in in vitro assays to search for drugs with the ability to disrupt the specific interaction between TIA-1 and the individual TIABPs. One example of such an application is outlined in Example II.

Because TIABP1 is an E2-type ubiquitin conjugating enzyme, it is likely to be involved in the ubiguitin-mediated degradation of TIA-1. The expression of toxic molecules such as TIA-1 must be closely regulated in the cell to prevent unwanted toxic effects. The present inventors have observed TIA-1 to be rapidly degraded in an ubiguit-independent manner in rabbit reticulocyte lysates. If a TIABP1 homolog is specifically involved in this process, then the regulation of the TIABP1 protein itself might be important in regulating the expression of TIA-1 as well. Using cDNAs reactive with TIABP1 and the polyclonal antisera reactive with the recombinant and natural TIABP1 protein, it will be possible to screen for transcriptional regulators that turn off the expression of this regulatory protein. Such a compound might be expected to result in increased expression of TIA-1 and, consequently, death of the cell. If compounds can be isolated which are preferentially taken up by rapidly growing cells, then such compounds could be used as anti-cancer agents. Because TIABP1 may also regulate the expression of the tumor suppressor gene p53, its decreased expression might also result in an increase in p53 protein, thus triggering apoptosis in a rapidly growing cell.

Purified recombinant TIABP2 protein and cDNAs encoding TIABP2 will allow, in an analogous fashion, screening for small drugs that can either disrupt or enhance the specific association between TIA-1 and TIABP2. Given the potential role of TIA-1 as a molecular toxin, such agents would be candidate anti-cancer drugs.

EXAMPLES

The present invention will now be described by reference to specific examples which are not meant to limit the invention in any way.

Example I

Isolation and Characterization of Two cDNA Clones Encoding TIA-1 Binding Proteins TIABP1 and TIABP2

The yeast expression vector PVA424 was digested with the restriction enzymes EcoR1 and BamH1 which cut within the multilinker region following the GAL4 DNA binding domain. The linearized vector was isolated by electrophoresis in a 1% low-melt agarose gel, after which the band was visualized by transillumination and excised from the gel. The cDNA encoding p40-TIA-1 was excised from the pSP65(λ269.4) vector by a double digestion with BstEII and BamHI. After electrophoretic separation on a 1% low-melt agarose gel, the smaller piece of linear DNA was excised from the gel. The two excised DNA fragments were combined with a synthetic oligolinker of the sequence:

```
(EcoRI) AAGTCGTCG                    (SEQ ID NO:12)
            GCAGCCATTG (BstEII)      (SEQ ID NO:13)
``` encoding an EcoR1 site at the upstream and a BstEII site at the downstream end. Following ligation, the full-length plasmid designated PMA424(p40-TIA-1) was isolated, expanded and purified.

Transformation of yeast strain GGY::171 with this recombinant plasmid was achieved by the lithium acetate method as described in *Nucleic Acid Research*, (1991), 19: 5791. Following selection on SC-his dropout plates, individual transformants were analyzed for their expression of the p40-TIA-1-Gal4 DNA binding domain fusion protein as shown in FIG. 1. Lysates from yeast transformed with the recombinant p40-GAL4 DNA binding domain contained a protein migrating at approximately 65 kD which was recognized by both poly(U)-agarose and by a monoclonal antibody reactive with TIA-1. Conversely, lysates from yeast cells transformed with vectors encoding the GAL4 DNA binding domain alone did not contain this immunoreactive material. In both cases, yeast cell lysates were prepared using 2% TRITON X-100, 100 mM NaCl, 100 mM Tris HCl pH 8.0, 1 mM EDTA. Following affinity precipitation using either poly(U)-agarose or SEPHAROSE immobilized anti-TIA-1 antibodies, precipitates were separated on a 10% SDS polyacrylamide gel and transferred to nitrocellulose. Individual blots were then probed with the monoclonal antibody reactive with TIA-1 and developed using the ECL method.

Figure 2B:
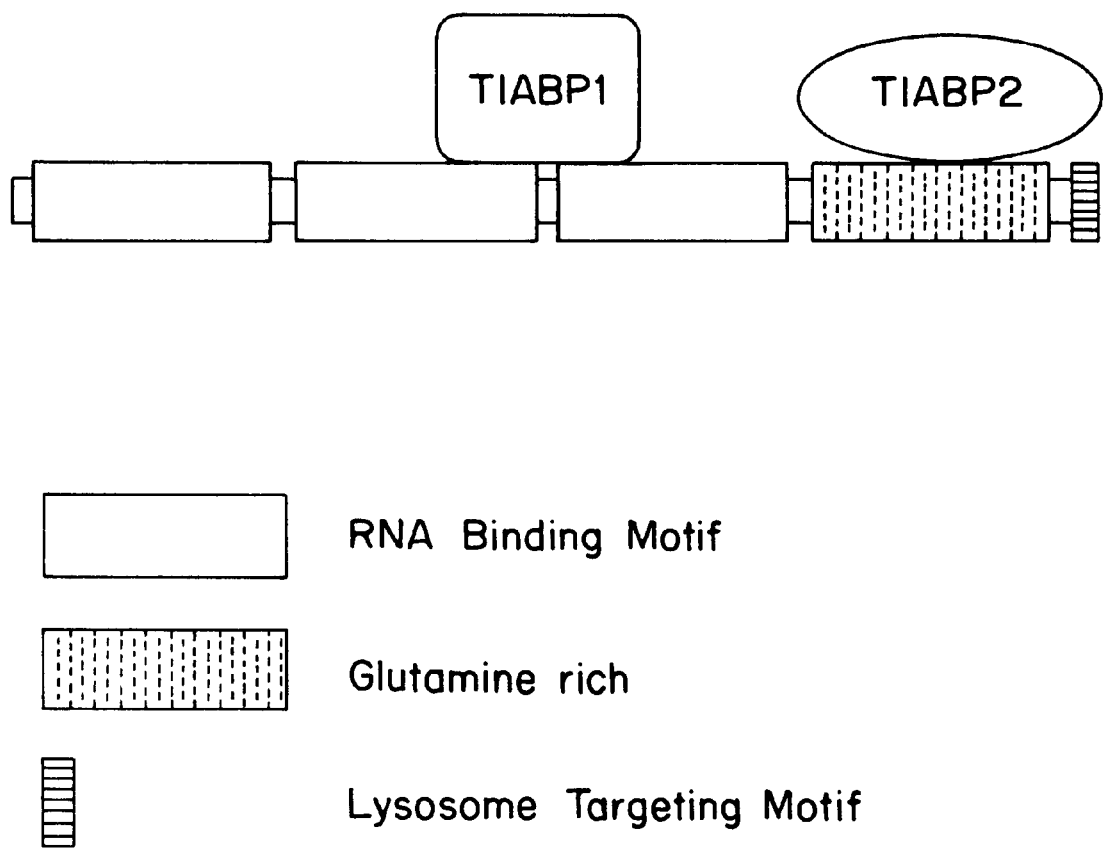
FIG. 2B is a schematic representation of how TIABP1 and TIABP2 are believed to interact with the RNA binding domains and the carboxy-terminal auxiliary domain, respectively, of TIA-1.
Figure 7:
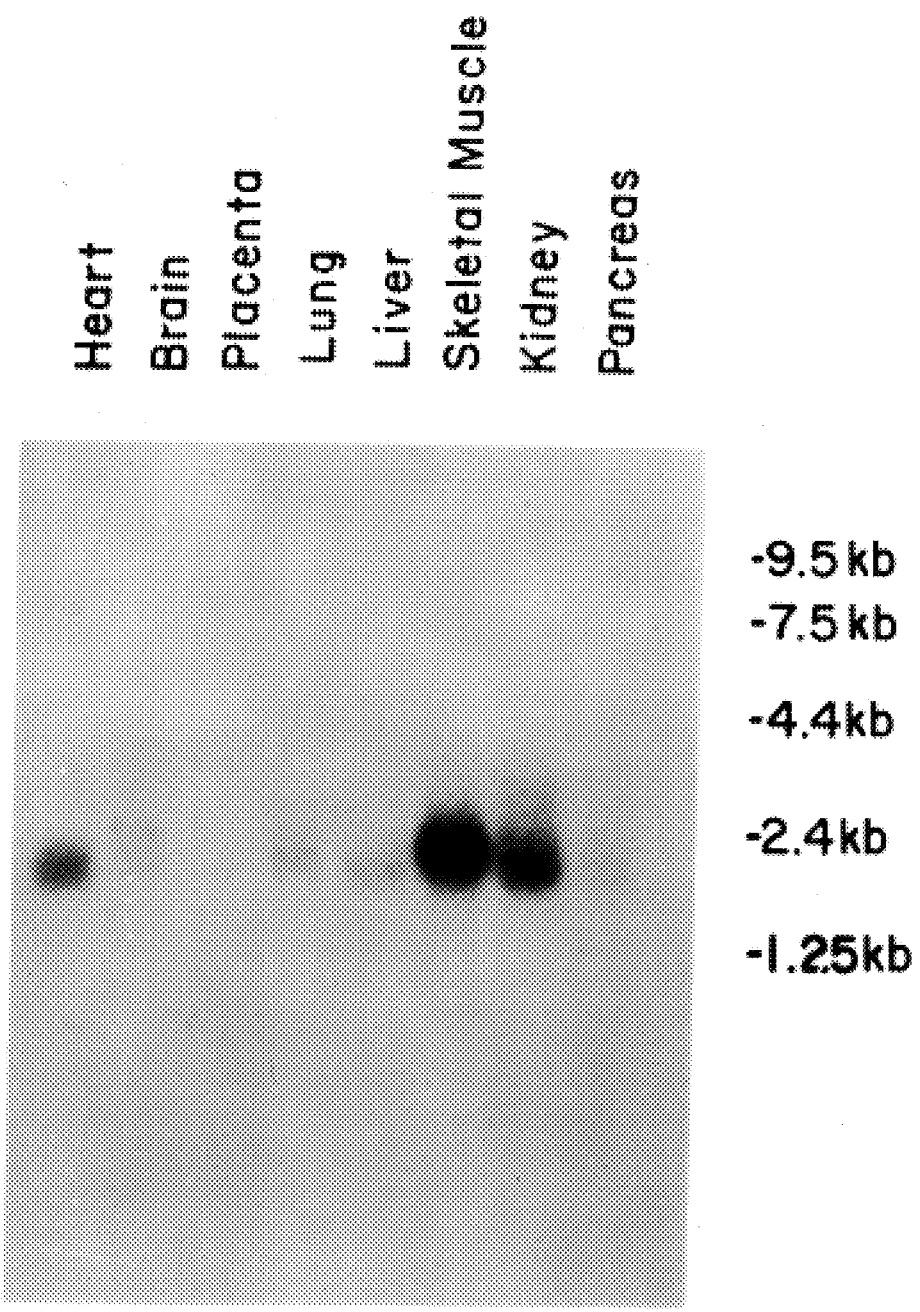
FIG. 7 is a Northern blotting analysis that shows the expression of mRNAs encoding TIABP2 in various tissues. Poly(A) mRNA extracted from the indicated human tissues was separated on a 1% formaldehyde agarose gel prior to transferring to nitrocellulose. The blot was then probed with a complete cDNA encoding TIABP2. The relative migrations of RNA size markers are shown on the left.

The identification of cDNAs encoding TIA-1 binding proteins was then accomplished by co-transforming GGY::171 cells with PMA424(p40-TIA-1) and a cDNA library prepared from poly(A) RNA from human B cells from which cDNA was transcribed and cloned into the XhoI site of the pSE1107 vector. In the cDNA library, individual cDNAs were expressed as fusion proteins consisting of the GAL4 activation domain (residues 768–881) at the amino terminus and peptides encoded by individual cDNAs at the carboxyl terminus as diagrammed in FIG. 2A. Following cotransfection, cells were plated on SC-Leu-His dropout medium plates to select for double transformants. After three days at 30° Celsius, yeast colonies were replica plated to Sc-Leu-His dropout medium plates containing X-gal for selection of colonies expressing β-galactosidase. Positive colonies were selected and expanded. To isolate DNA from positive colonies, individual colonies were suspended in 100 µl of lysis buffer (2% TRITON X-100, 1% SDS, 100 mM NaCl, 100 mM Tris HCl pH 8.0, 1 mM EDTA), plus 100 µl of phenol/chloroform/isoamyl alcohol. After the addition of 0.1 gram of glass beads, these preparations were vortexed for two minutes, centrifuged in an Eppendorf centrifuge, and the supernatants were transferred to a clean Eppendorf tube. DNA was then precipitated by the addition of 3 M NaOAc, 250 µl ethanol. After resuspending the precipitated DNA in 4 µl TE buffer, 2 µl of this DNA was used to transform an E. coli LeuB⁻ strain (W921) by electroporation. DNA was isolated from E. coli transformants and digested with XhoI to liberate the cDNA inserts. After screening 400,000 double transformants of yeast cells, four positive colonies were obtained. Three of these encoded TIABP1 (1.2 kb insert), and one encoded TIABP2 (1.5 kb insert).

The nucleotide sequence (SEQ ID NO:1) and deduced amino acid sequence (SEQ ID NO:2) of TIABP1 are shown in FIG. 3. The nucleotide sequence (SEQ ID NO:3) and deduced amino acid sequence (SEQ ID NO:4) of TIABP2 are shown in FIG. 4.

GST Fusion Proteins

The 1.8 kb cDNA encoding TIABP2 was cloned into the EcoR1 site of the polylinker region of pGEX-3X using oligonucleotide linkers. These constructs were designed to express TIABP2 as a fusion protein with glutathione-S-transferase. An individual colony of E. coli (DH5) bacterial cells transformed with pGEX-3X/TIABP2 was used to inoculate 25 ml of LB media containing ampicillin (100 µg/ml). Cultures were grown with shaking at 37° C. overnight. 20 ml of the overnight culture was used to inoculate 800 ml of 2X YT medium containing 100 µg/ml ampicillin. Cultures were shaken at 37° C. until the O.D.$_{600}$ was approximately 0.6. At that time, IPTG was added to 0.2 mM final concentration and cultures were incubated for a further 3 hours at 30° C. Cells were then harvested by centrifugation at 4,000 rpm for 10 min. Pellets were suspended in 10 ml of PBS containing 1 mM EDTA, 1 mM DTT, 0.1 mM PMSF. Cells were then disrupted by sonication, and centrifuged at 40,000 rpm for 30 min at 4° C. to remove insoluble debris. Supernatants were applied to a column of glutathione-agarose beads (Sigma Chemical Company) and incubated for 30 min at 4° C. Beads were then washed 3× with 10 ml of PBS containing 1 mM EDTA, 1 mM DTT, 0.1 mM PMSF, and 2× with PBS alone. Individual fusion proteins were then eluted by competition with glutathione applied at 10 mM final concentration in 50 mM Tris, pH 8.0. The eluate was dialyzed against 50 mM Tris, 150 mM NaCl, 1 mM DTT, pH 8.0, to remove free glutathione. The purified fusion protein was analyzed on a 10% SDS polyacrylamide gel by staining with Coomassie blue. Fusion proteins were also analyzed by immunoblotting using rabbit polyclonal antisera raised against recombinant TIABP2.

Northern Blot Analysis

Nitrocellulose filters containing poly(A)+RNA from the indicated tissues were purchased from Clontech. Each filter was prehybridized in 50% formamide, 5× SSC, 25 mM potassium phosphate buffer (pH 7.4), 5× Denhart's and 50 mg/ml denatured salmon sperm DNA for 4 hours at 42° C. The 1.8 kb TIABP2 insert DNA was $^{32}$P-labeled by nick translation, diluted in the above solution, and hybridized to the filter for 24 hours at 42° C. The filter was then washed twice with 1× SSC containing 0.1% SDS and twice with 0.1× SSC containing 0.1% SDS prior to autoradiographic exposure.

Cos Cell Transfections

Cos cells were transfected with the plasmid pMT-2 containing the indicated insert DNA using the diethylaminoethyl dextran method as described by Sambrook, J., E. F. Fritsch, and T. Maniatis. 1989. Molecular Cloning. A Laboratory Manual. After three days of culture, transfected cells were solubilized with lysis buffer, and used in the immunoprecipitation and immunoblotting experiments.

Immunoprecipitations

The indicated cell types were lysed in NP-40 lysis buffer (1% NP-40, 150 mN NaCl, 1 mM EDTA, 1 mM phenylmethylsulfonyl fluoride, 50 mM Tris HCl, pH 8.0), and immunoprecipitations were performed using methods previously described: Anderson, P., et al (1990), "A monoclonal antibody reactive with a 15 kD cytoplasmic granule-associated protein defines a subpopulation of CD8+ T-lymphocytes", Journal of Immunology, 144: 574. Individual immunoprecipitates were separated on a 10% SDS polyacrylamide gel, transferred to nitrocellulose or PVDF filters and revealed and developed using polyclonal and monoclonal antibodies as described below.

Immunoblot Analysis

Immunoblotting analysis was carried out as previously described {Anderson, P. et al, (1990), "A monoclonal antibody reactive with a 15-kDa cytoplasmid granule-associated protein defines a subpopulation of CD8+ T lymphocytes", J. Immunol. 144: 574}. Immunoblots were developed using polyclonal or monoclonal antibodies reactive with TIABP2, followed by horse radish peroxidase conjugate protein A/G. Blots were revealed using the ECL detection system (Renaissance, DuPont, Boston, Mass.).

Example II

Method to Screen for Inhibitors of TIABP1:P53 or TIA-1 Interactions

Existing technology can be used to screen for drugs that inhibit the interaction between TIABP1 and its substrates. In the case of p53:TIABP1 interactions, such drugs might have anti-tumor activity directed against HPV-associated cancers expressing low levels of p53. In the case of TIA-1:TIABP1 interactions, such drugs might be beneficial in treating autoimmune diseases in which CTLs are involved in tissue destruction. Examples include graft vs. host disease, allograft rejection following organ transplantation, autoimmune thyroiditis, and autoimmune diabetes melitis.

A variation of the two hybrid system adapted for mammalian cells to screen for inhibitors of TIABP1:TIA-1, TIABP1:p53, and TIABP2:TIA-1 interactions can be employed. The method to be employed is schematized in FIGS. 6A and 6B. The general method involves the construction of plasmids encoding chimeric fusion proteins whose interaction triggers the transcription of a reporter gene in a mammalian cell. One of several promoters, reporter genes, DNA binding proteins, and transactivation domains can be used. In one example (FIG. 6A), plasmids encoding chimeric fusion proteins between: i) the GAL4 DNA-binding domain and TIA-1, and ii) TIABP1 and the VP16 activation domain (411–455) are used to activate transcription of the gene for secreted alkaline phosphatase under control of the GAL4 promoter. In this example, the interaction between TIA-1 and TIABP1 results in constitutive expression of secreted alkaline phosphatase. By culturing these cells in the presence of candidate inhibitors of the TIA-1:TIABP1 interaction, cell supernatants can be screened for decreased alkaline phosphatase activity. In another example (FIG. 6B), plasmids encoding fusion proteins between: i) the tetracycline repressor and TIA-1, and ii) TIABP1 and the V16 transactivation domain (411–455) are used to transform cells expressing a toxin gene such as ricin A under control of a tetracycline promoter. Cells are then cultured in the presence of tetracycline, which prevents the interaction between the tetR and the tet promoter. At confluence, tetracycline is removed and individual drugs are added. The interaction between TIA-1 and TIABP1 results in transcription of ricin A, resulting in cell death. Cells cultured in the presence of drugs which block the interaction between TIA-1 and TIABP1 will survive. A vital dye can be used to screen for viable cells.

Example III

Purification and Isolation of TIABP1 and TIABP2 cDNAS encoding TIABP1 and TIABP2 were cloned into one EcoR1 site of the polylinker region of pGEX-3X using oligonucleotide linkers. These constructs were designed to express both TIABP1 and TIABP2 as fusion proteins with glutathione-S-transferase. Each recombinant plasmid was transfected into E. coli (DH5) and fusion proteins were induced by the addition of IPTG. Individual colonies of DH5 bacterial cells transformed with either pGEX-3X/TIABP1 or pGEX-3X/TIABP2 were used to inoculate 25 ml of LB media containing ampicillin (100 $\mu$g/ml). Cultures were grown with shaking at 37° C. overnight. 20 ml of the overnight culture was used to inoculate 800 ml of 2× YT medium containing 100 $\mu$g/ml ampicillin. Cultures were shaken at 37° C. until the O.D.$_{600}$ was approximately 0.6. At that time, IPTG was added to 0.2 mM final concentration and cultures were incubated for a further 3 hours at 30° C. Cells were then harvested by centrifugation at 4,000 rpm for 10 min Pellets were suspended in 10 ml of PBS containing 1 mM EDTA, 1 mM DTT, 0.1 mM PMSF. Cells were then disrupted by sonication, and centrifuged at 40,000 rpm for 30 min at 4° C. to remove insoluble debris. Supernatants were applied to a column of glutathione-agarose beads (Sigma Chemical Company) and incubated for 30 min at 4° C. Beads were then washed 3× with 10 ml of PBS containing 1 mM EDTA, 1 mM DTT, 0.1 mM PMSF, and 2× with PBS alone. Individual fusion proteins were then eluted by competition with glutathione applied at 10 mM final concentration in 50 mM Tris, pH 8.0. The eluate was dialyzed against 50 mM Tris, 150 mM NaCl, 1 mM DTT, pH 8.0, to remove free glutathione. The purified fusion protein was analyzed on a 10% SDS polyacrylamide gel by staining with Coomassie blue. Fusion proteins were also analyzed by immunoblotting using rabbit polyclonal antisera raised against recombinant TIA-1 and recombinant TIAR.

While the invention has been described in detail and with reference to specific embodiments thereof, it will be apparent to one skilled in the art that various changes and modifications can be made therein without departing from the spirit and scope thereof.

What is claimed is:

1. Isolated cDNA comprising a sequence that encodes a polypeptide that binds TIA-1 in a double transformation under standard conditions, wherein: said cDNA is isolated from human cells; and said polypeptide co-precipitates bound to TIA-1, using a monoclonal antibody that is immunologically reactive with TIA-1.

2. The isolated cDNA of claim 1, wherein said sequence encodes a polypeptide that binds the RNA binding domain of TIA-1.

3. The isolated cDNA of claim 1, that hybridizes:
   (a) to an at least six- to twenty-nucleotide segment having a sequence complementary to an at least six- to twenty-nucleotide segment of SEQ ID NO:1; and
   (b) in 50% formamide and at least at 20° C.

4. Isolated cDNA comprising a sequence that encodes a polypeptide that binds TIA-1, wherein said sequence is SEQ ID NO:1.

5. The isolated cDNA of claim 1, that hybridizes:
   (a) to an at least six- to twenty-nucleotide segment having a sequence complementary to an at least six- to twenty-nucleotide segment of the sequence from nucleotide 172 to nucleotide 645 of SEQ ID NO:1; and
   (b) in 50% formamide and at least at 20° C.

6. Isolated cDNA comprising a sequence that encodes a polypeptide that binds TIA-1, wherein said sequence is the sequence from nucleotide 172 to nucleotide 645 of SEQ ID NO:1.

7. The isolated cDNA of claim 1, wherein said sequence encodes a polypeptide that binds the carboxy-terminal auxiliary domain of TIA-1.

8. The isolated cDNA of claim 1, that hybridizes:
   (a) to an at least six- to twenty-nucleotide segment having a sequence complementary to an at least six- to twenty-nucleotide segment of SEQ ID NO:3; and
   (b) in 50% formamide and at least at 20° C.

9. Isolated cDNA comprising a sequence that encodes a polypeptide that binds TIA-1, wherein said sequence is SEQ ID NO:3.

10. The isolated cDNA of claim 1, that hybridizes:
    (a) to an at least six- to twenty-nucleotide segment having a sequence complementary to an at least six- to twenty-nucleotide segment of the sequence from nucleotide 265 to nucleotide 1688 of SEQ ID NO:3; and
    (b) in 50% formamide and at least at 20° C.

11. Isolated cDNA comprising a sequence that encodes a polypeptide that binds TIA-1, wherein said sequence is the sequence from nucleotide 265 to nucleotide 1668 of SEQ ID NO:3.

12. Isolated cDNA comprising a sequence that encodes a polypeptide that binds p40-TIA-1 or an isoform of p40-TIA-1 in a double transformation under standard conditions, wherein: said cDNA is isolated from human cells; said polypeptide co-precipitates bound to p40-TIA-1 or said isoform of p40-TIA-1, using a monoclonal antibody that is immunologically reactive with p40-TIA-1; and said isoform of p40-TIA-1 is immunologically reactive with said monoclonal antibody.

13. The isolated cDNA of any one of claims 1, 7, 8, 9, 10, 11, or 12, wherein said polypeptide is immunologically reactive with monoclonal antibody 2B5 produced by a hybridoma designated ATCC #HB-11721.

14. Isolated cDNA that hybridizes:
    (a) to an at least six- to twenty-nucleotide segment having a sequence complementary to an at least six- to twenty-nucleotide segment of SEQ ID NO:1;
    (b) in 50% formamide, at 42° C., or in aqueous solution, at 68° C.;
    (c) said cDNA encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

15. Isolated cDNA that hybridizes:
    (a) to an at least six- to twenty-nucleotide segment having a sequence complementary to an at least six- to twenty-nucleotide segment of SEQ ID NO:3;
    (b) in 50% formamide, at 42° C., or in aqueous solution, at 68° C.;
    (c) said cDNA encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

16. Isolated cDNA that hybridizes:
    (a) to a sequence complementary to the coding sequence of SEQ ID NO:1;
    (b) in 50% formamide, at 20° C.;
    (c) said cDNA encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

17. Isolated cDNA that hybridizes:
    (a) to a sequence complementary to the coding sequence of SEQ ID NO:3;
    (b) in 50% formamide, at 20° C.;
    (c) said cDNA encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

18. Purified nucleic acid comprising a sequence that encodes a polypeptide that binds TIA-1 in a double transformation under standard conditions, wherein: said nucleic acid is purified from human cells; and said polypeptide co-precipitates bound to TIA-1, using a monoclonal antibody that is immunologically reactive with TIA-1.

19. Purified nucleic acid comprising a sequence that encodes a polypeptide that binds p40-TIA-1 or an isoform of p40-TIA-1 in a double transformation under standard conditions, wherein: said nucleic acid is isolated from human cells; said polypeptide co-precipitates bound to p40-TIA-1 or said isoform of p40-TIA-1, using a monoclonal antibody that is immunologically reactive with said p40-TIA-1; and said isoform of p40-TIA-1 is immunologically reactive with said monoclonal antibody.

20. The purified nucleic acid of any one of claims 18 or 19, wherein said polypeptide is immunologically reactive with monoclonal antibody 2B5 produced by a hybridoma designated ATCC #HB-11721.

21. Purified nucleic acid that hybridizes:
    (a) to an at least six- to twenty-nucleotide segment of SEQ ID NO:1, or to an at least six- to twenty-nucleotide segment having a sequence complementary to an at least six- to twenty-nucleotide segment of SEQ ID NO:1;
    (b) in 50% formamide, at 42° C. or in aqueous solution, at 68° C.;
    (c) said nucleic acid encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

22. Purified nucleic acid that hybridizes:
    (a) to an at least six- to twenty-nucleotide segment of SEQ ID NO:3, or to an at least six- to twenty-nucleotide segment having a sequence complementary to an at least six- to twenty-nucleotide segment of SEQ ID NO:3;
    (b) in 50% formamide, at 42° C., or in aqueous solution, at 68° C.;
    (c) said nucleic acid encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

23. Purified nucleic acid that hybridizes:
    (a) to the coding sequence or sequence complementary to the coding sequence of SEQ ID NO:1;
    (b) in 50% formamide, at 20° C.;
    (c) said nucleic acid encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

24. Purified nucleic acid that hybridizes:
    (a) to the coding sequence or sequence complementary to the coding sequence of SEQ ID NO:3;
    (b) in 50% formamide, at 20° C.;
    (c) said nucleic acid encodes a polypeptide that binds TIA-1 in a double transformation under standard conditions, and is isolated from human cells; and
    (d) said polypeptide co-precipitates bound to TIA-1, using a monoclonal antibody that is immunologically reactive with TIA-1.

25. A purified preparation of a vector, said vector comprising an isolated cDNA comprising a sequence that encodes a polypeptide or a fragment of said polypeptide that binds TIA-1 in a double transformation under standard conditions, wherein: said cDNA is isolated from human cells; and said polypeptide or said fragment co-precipitates bound to TIA-1, using a monoclonal antibody that is immunologically reactive with TIA-1.

26. A purified preparation of a vector, said vector comprising an isolated cDNA comprising a sequence that encodes a polypeptide that binds p40-TIA-1 or an isoform of p40-TIA-1 in a double transformation under standard conditions, wherein: said cDNA is isolated from human cells; said polypeptide co-precipitates bound to p40-TIA-1 or said isoform of p40-TIA-1, using a monoclonal antibody that is immunologically reactive with p40-TIA-1; and said isoform of p40-TIA-1 is immunologically reactive with said monoclonal antibody.

27. The purified preparation of a vector of claims 25 or 26, wherein said polypeptide is immunologically reactive with monoclonal antibody 2B5 produced by a hybridoma designated ATCC #HB-11721.

28. A plasmid deposited as ATCC #69371.

29. A plasmid deposited as ATCC #69372.

30. An isolated cell transformed with an isolated cDNA comprising a sequence that encodes a polypeptide that binds TIA-1 in a double transformation under standard conditions, wherein: said cDNA is isolated from human cells; and said polypeptide co-precipitates bound to TIA-1, using a monoclonal antibody that is immunologically reactive with TIA-1.

31. An isolated cell transformed with an isolated cDNA comprising a sequence that encodes a polypeptide that binds p40-TIA-1 or an isoform of p40-TIA-1 in a double transformation under standard conditions, wherein: said cDNA is isolated from human cells; said polypeptide co-precipitates bound to P40-TIA-1 or said isoform of p40-TIA-1, using a monoclonal antibody that is immunologically reactive with p40-TIA-1; and said isoform of p40-TIA-1 is immunologically reactive with said monoclonal antibody.

32. The isolated cell of claim 30 or 31, wherein said polypeptide is immunologically reactive with monoclonal antibody 2B5 produced by a hybridoma designated ATCC #HB-11721.

33. A method of producing a polypeptide, wherein said method comprises culturing the isolated cell of claim 30 or 31 under conditions permitting the expression of said isolated cDNA and recovering said polypeptide encoded by said isolated cDNA.

34. Isolated cDNA comprising SEQ ID NO:1.

35. Isolated cDNA comprising the sequence from nucleotide 172 to nucleotide 645 of SEQ ID NO:1.

36. Isolated cDNA comprising SEQ ID NO:3.

37. Isolated cDNA comprising the sequence from nucleotide 265 to nucleotide 1668 of SEQ ID NO:3.

38. Isolated cDNA that hybridizes:
    (a) to an at least six- to twenty-nucleotide segment having a sequence complementary to an at least six- to twenty-nucleotide segment of SEQ ID NO:1;
    (b) in 50% formamide, at 42° C., or in aqueous solution, at 68° C.;
    (c) said cDNA encodes a polypeptide that binds TIA-1 in a double transformation under standard conditions, and is isolated from mammalian, Drosophila or yeast cells; and
    (d) said polypeptide co-precipitates bound to TIA-1, using a monoclonal antibody that is immunologically reactive with TIA-1.

39. The isolated cDNA of claim 38, wherein said cells are mammalian cells.

40. Isolated cDNA that hybridizes:
    (a) to an at least six- to twenty-nucleotide segment having a sequence complementary to an at least six- to twenty-nucleotide segment of SEQ ID NO:3;

(b) in 50% formamide, at 42° C., or in aqueous solution, at 68° C.;

(c) said cDNA encodes a polypeptide that binds TIA-1 in a double transformation under standard conditions, and is isolated from mammalian, Drosophila or yeast cells; and (d) said polypeptide co-precipitates bound to TIA-1, using a monoclonal antibody that is immunologically reactive with TIA-1.

41. The isolated cDNA of claim 40, wherein said cells are mammalian cells.

42. Isolated cDNA that hybridizes:

(a) to a sequence complementary to the coding sequence of SEQ ID NO:1;

(b) in 50% formamide, at 20° C.;

(c) said cDNA encodes a polypeptide that binds TIA-1 in a double transformation under standard conditions, and is isolated from mammalian Drosophila or yeast cells; and (d) said polypeptide co-precipitates bound to TIA-1, using a monoclonal antibody that is immunologically reactive with TIA-1.

43. The isolated cDNA of claim 42, wherein said cells are mammalian cells.

44. Isolated cDNA that hybridizes:

(a) to a sequence complementary to the coding sequence of SEQ ID NO:3;

(b) in 50% formamide, at 20° C.;

(c) said cDNA encodes a polypeptide that binds TIA-1 in a double transformation under standard conditions, and is isolated from mammalian Drosophila or yeast cells; and (d) said polypeptide co-precipitates bound to TIA-1, using a monoclonal antibody that is immunologically reactive with TIA-1.

45. The isolated cDNA of claim 44, wherein said cells are mammalian cells.

46. Purified nucleic acid that hybridizes:

(a) to an at least six- to twenty-nucleotide segment of SEQ ID NO:1, or to an at least six- to twenty-nucleotide segment having a sequence complementary to an at least six- to twenty-nucleotide segment of SEQ ID NO:1;

(b) in 50% formamide, at 42° C., or in aqueous solution, at 68° C.;

(c) said nucleic acid encodes a polypeptide that binds TIA-1 in a double transformation under standard conditions, and is isolated from mammalian, Drosophila or yeast cells; and (d) said polypeptide co-precipitates bound to TIA-1, using a monoclonal antibody that is immunologically reactive with TIA-1.

47. The purified nucleic acid of claim 46, wherein said cells are mammalian cells.

48. Purified nucleic acid that hybridizes:

(a) to an at least six- to twenty-nucleotide segment of SEQ ID NO:3, or to an at least six- to twenty-nucleotide segment having a sequence complementary to an at least six- to twenty-nucleotide segment of SEQ ID NO:3;

(b) in 50% formamide, at 42° C., or in aqueous solution, at 68° C.;

(c) said nucleic acid encodes a polypeptide that binds TIA-1 in a double transformation under standard conditions, and is isolated from mammalian, Drosophila or yeast cells; and (d) said polypeptide co-precipitates bound to TIA-1, using a monoclonal antibody that is immunologically reactive with TIA-1.

49. The purified nucleic acid of claim 48, wherein said cells are mammalian cells.

50. Purified nucleic acid that hybridizes:

(a) to a coding sequence or sequence complementary to the coding sequence of SEQ ID NO:1;

(b) in 50% formamide, at 20° C.;

(c) said nucleic acid encodes a polypeptide that binds TIA-1 in a double transformation under standard conditions, and is isolated from mammalian, Drosophila or yeast cells; and (d) said polypeptide co-precipitates bound to TIA-1, using a monoclonal antibody that is immunologically reactive with TIA-1.

51. The purified nucleic acid of claim 50, wherein said cells are mammalian cells.

52. Purified nucleic acid that hybridizes:

(a) to a coding sequence or sequence complementary to the coding sequence of SEQ ID NO:3;

(b) in 50% formamide, at 20° C.;

(c) said nucleic acid encodes a polypeptide that binds TIA-1 in a double transformation under standard conditions, and is isolated from mammalian, Drosophila or yeast cells; and (d) said polypeptide co-precipitates bound to TIA-1, using a monoclonal antibody that is immunologically reactive with TIA-1.

53. The purified nucleic acid of claim 52, wherein said cells are mammalian cells.

* * * * *